United States Patent
Kobayashi

(10) Patent No.: US 10,473,656 B2
(45) Date of Patent: Nov. 12, 2019

(54) TESTING DEVICE INCLUDING RESIN LAYER, TESTING KIT, TRANSFER MEMBER, TESTING DEVICE FABRICATION METHOD, AND TESTING METHOD

(71) Applicant: Rie Kobayashi, Shizuoka (JP)

(72) Inventor: Rie Kobayashi, Shizuoka (JP)

(73) Assignee: Ricoh Company, Ltd., Tokyo (JP)

(*) Notice: Subject to any disclaimer, the term of this patent is extended or adjusted under 35 U.S.C. 154(b) by 398 days.

(21) Appl. No.: 15/121,915

(22) PCT Filed: Feb. 27, 2015

(86) PCT No.: PCT/JP2015/056579
§ 371 (c)(1),
(2) Date: Aug. 26, 2016

(87) PCT Pub. No.: WO2015/129924
PCT Pub. Date: Sep. 3, 2015

(65) Prior Publication Data
US 2017/0067892 A1    Mar. 9, 2017

(30) Foreign Application Priority Data

Feb. 28, 2014  (JP) ................. 2014-039392
Jan. 30, 2015  (JP) ................. 2015-017565
Feb. 26, 2015  (JP) ................. 2015-036766

(51) Int. Cl.
*G01N 33/558*  (2006.01)
*G01N 33/545*  (2006.01)

(52) U.S. Cl.
CPC ......... *G01N 33/558* (2013.01); *G01N 33/545* (2013.01); *G01N 2333/59* (2013.01)

(58) Field of Classification Search
None
See application file for complete search history.

(56) References Cited

U.S. PATENT DOCUMENTS 4,258,001 A * 3/1981 Pierce ............... G01N 31/22
                                              422/400
5,071,746 A * 12/1991 Wilk ............... G01N 33/54366
                                              422/414
5,104,811 A    4/1992 Berger et al.
(Continued)

FOREIGN PATENT DOCUMENTS

CN      101676722 A     3/2010
JP         3552272      5/2004
(Continued)

OTHER PUBLICATIONS

Machine translation of CN101676722 retrieved on Jan. 29, 2019 from Patent Translate (7 pages total).*
(Continued)

*Primary Examiner* — Christine Foster
(74) *Attorney, Agent, or Firm* — Oblon, McClelland, Maier & Neustadt, L.L.P.

(57) ABSTRACT

Provided is a testing device, including: a porous flow path member in which a flow path for flowing a sample is formed; and a resin layer provided at one position or a plurality of positions over the flow path member, wherein a reagent reactive with the sample is provided as a solid phase over a surface of the resin layer facing the flow path member.

11 Claims, 11 Drawing Sheets

(56) References Cited

U.S. PATENT DOCUMENTS

| | | | |
|---|---|---|---|
| 5,110,550 | A | 5/1992 | Schlipfenbacher et al. |
| 6,497,842 | B1 | 12/2002 | Takahashi et al. |
| 2003/0190759 | A1* | 10/2003 | Kawamura ...... G01N 33/54366 436/514 |
| 2008/0194013 | A1* | 8/2008 | Shida ............... G01N 33/54386 435/287.2 |
| 2011/0189792 | A1 | 8/2011 | Reinhartz et al. |

FOREIGN PATENT DOCUMENTS

| | | |
|---|---|---|
| JP | 2006-284567 | 10/2006 |
| JP | 2007-255999 | 10/2007 |
| JP | 2007-327778 | 12/2007 |
| JP | 2010-038797 | 2/2010 |
| JP | 2010-256309 | 11/2010 |
| JP | 5207290 | 3/2013 |
| WO | WO 2015/041373 A1 | 3/2015 |

OTHER PUBLICATIONS

International Search Report dated Jun. 2, 2015 for counterpart International Patent Application No. PCT/JP2015/056579 filed Feb. 27, 2015.

Written Opinion of the International Preliminary Report on Patentability dated Mar. 10, 2016 for counterpart International Patent Application No. PCT/JP2015/056579 filed Feb. 27, 2015.

Combined Office Action and Search Report dated Dec. 12, 2017 in Chinese Patent Application No. 201580023632.2 (with English language translation), 25 pages.

Extended European Search Report dated Feb. 6, 2017 in Application No. 15755498.1.

Juan Su, et al., "Quantitative detection of human chorionic gonadotropin antigen via immunogold chromatographic test strips" Analytical Methods, XP055324977, vol. 6, 2014, pp. 450-455.

Office Action dated Jan. 22, 2019 in Japanese Patent Application No. 2015-036766.

* cited by examiner

Table 2

| Evaluation criteria | A | B | C | D |
|---|---|---|---|---|
| Images |  |  |  |  |

TESTING DEVICE INCLUDING RESIN LAYER, TESTING KIT, TRANSFER MEMBER, TESTING DEVICE FABRICATION METHOD, AND TESTING METHOD

TECHNICAL FIELD

The present invention relates to a testing device in which a flow path for flowing a sample is formed.

BACKGROUND ART

Conventionally, testing devices in which a flow path for flowing a sample is formed have been used for the purposes of testing samples such as blood, DNA, foods, or beverages. As an example of a testing device, there has been disclosed a testing device including: a sample pad as a liquid receiving portion for receiving a test liquid; a conjugate pad in which the test liquid supplied from the sample pad undergoes a reaction; and a membrane film for flowing the test liquid supplied from the conjugate pad (see PTL 1). The conjugate pad contains a labeled antibody obtained by labeling an antibody with a pigment or the like. When supplied with a test liquid from the sample pad, the conjugate pad lets any antigen contained in the test liquid react with the labeled antibody, and supplies them to the membrane film. On the other hand, an antibody (capture antibody) for capturing the antigen is previously applied over a detection portion of the membrane film. The antigen contained in the test liquid supplied from the conjugate pad is captured at the detection portion in the state of being conjugated with the labeled antibody. As a result, a color is developed at the detection portion, which makes it possible to measure the antigen contained in the test liquid qualitatively or quantitatively by visually observing or measuring the degree of the color development.

In use of a testing kit for the purposes of simple in-vitro diagnoses or the like, it is requested to save the time taken for the testing in order to reduce the burdens on the doctor, the patient, etc. Hence, PTL 1 discloses adjusting a water absorption speed of a synthetic fiber constituting the conjugate pad, to thereby increase a spreading speed of the test liquid and save the testing time.

CITATION LIST

Patent Literature

PTL 1 Japanese Patent Application Laid-Open (JP-A) No. 2010-256309

SUMMARY OF INVENTION

Technical Problem

However, in the conventional testing devices, reagents such as a labeled antibody and a capture antibody, and reagents such as a labeling indicator and a detection indicator are provided as a solid phase over the fiber of a flow path member or the like. Therefore, when a material of the flow path member is selected arbitrarily in order to increase the spreading speed of a sample, there may occur problems that the flow path member has an excessively strong interaction with the reagents such as the labeled antibody and the labeling indicator and cannot diffuse the reagents, or that the flow path member has an excessively weak interaction with the reagents such as the capture antibody and the detection indicator and cannot fix the captured sample.

Further, a test line and a control line are formed by directly applying a liquid in which a capture antibody is dissolved over a flow path member made of a hydrophilic porous material. Therefore, the capture antibody is present in the hydrophilic porous material in a diffused state. However, colorant from labeling particles such as gold colloid particles that are bound with the capture antibody present in the hydrophilic porous material cannot be sensed actually, because light scattering occurs. That is, there has been a significant problem that much of the capture antibody is not utilized effectively.

Solution to Problem

A testing device of the present invention as a solution to the problems described above includes:

a porous flow path member in which a flow path for flowing a sample is formed; and a resin layer provided at one position or a plurality of positions over the flow path member, wherein a reagent reactive with the sample is provided as a solid phase over a surface of the resin layer facing the flow path member.

Advantageous Effects of Invention

With the testing device of the present invention, it is possible to adjust the strength of interaction between the resin layer and the reagent, by selecting a resin depending on the reagent to be used. Therefore, even when the flow path member is selected arbitrarily depending on the purpose, it is easy to control release and fixing of the reagent.

DESCRIPTION OF EMBODIMENTS

An embodiment of the present invention will be described below with reference to the drawings.

<<<Overall Configuration of Embodiment>>>

Figure 1:
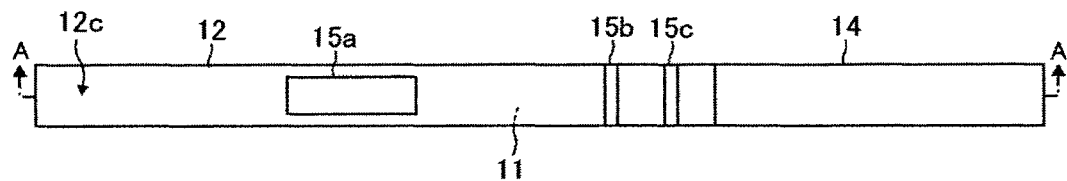
FIG. 1 is a top plan view of a testing device according to an embodiment of the present invention.
Figure 2:
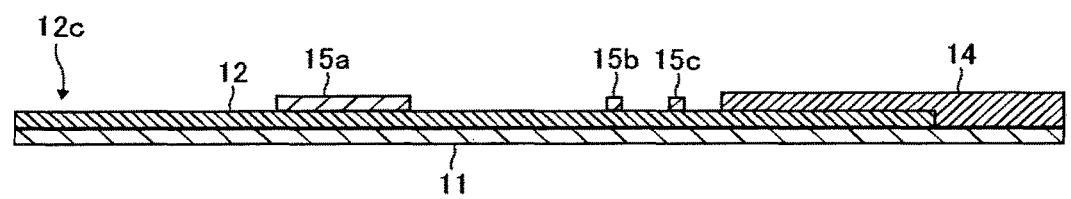
FIG. 2 is a cross-sectional diagram of a testing device according to an embodiment of the present invention.
Figure 3:
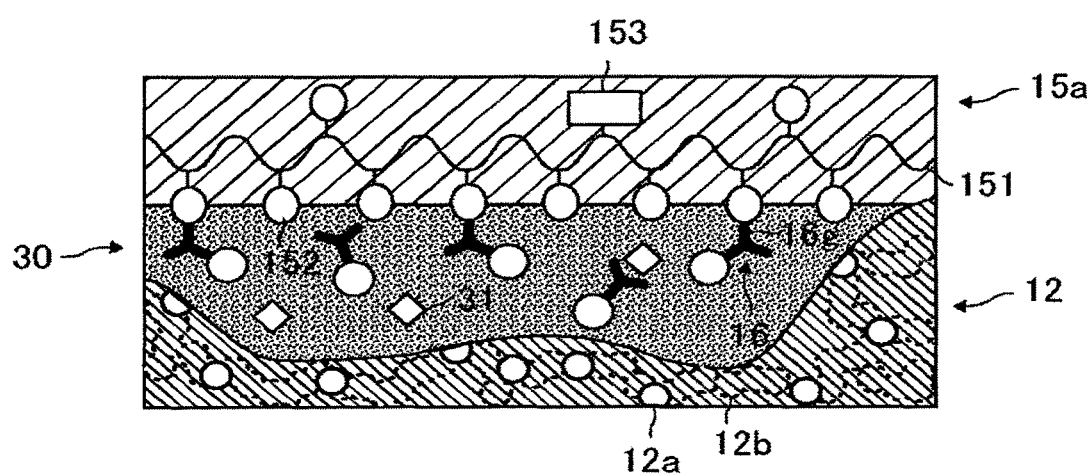
FIG. 3 is a cross-sectional diagram of a testing device, showing a portion at which a flow path member and a resin layer face each other.
Figure 4A:
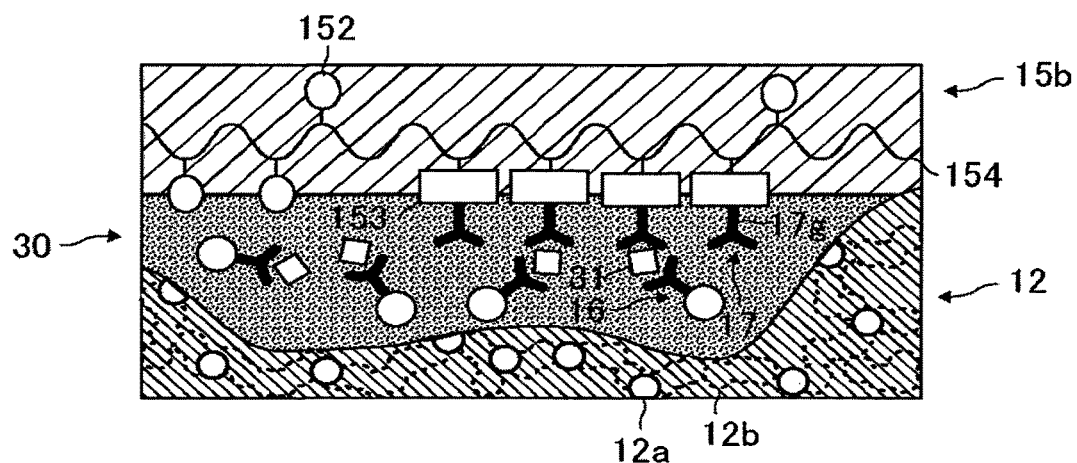
FIG. 4A is a cross-sectional diagram of a testing device, showing a portion at which a flow path member and a resin layer face each other.
Figure 4B:
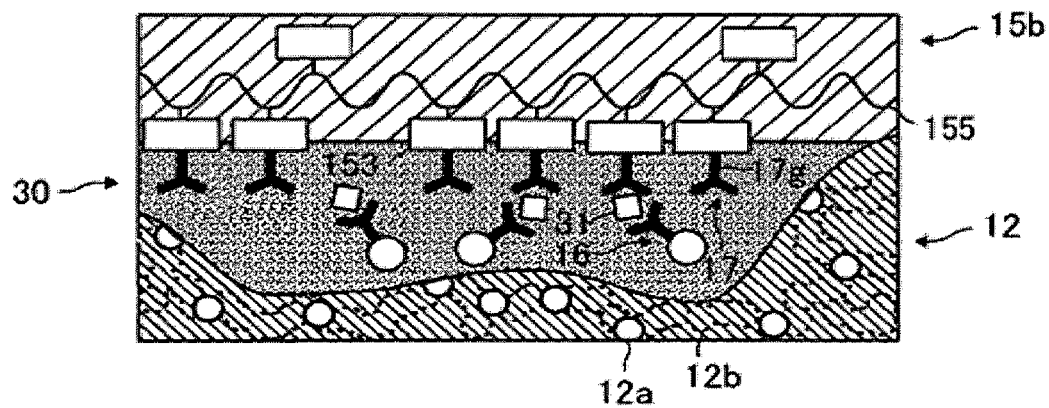
FIG. 4B is a cross-sectional diagram of a testing device, showing a portion at which a flow path member and a resin layer face each other.
Figure 5A:
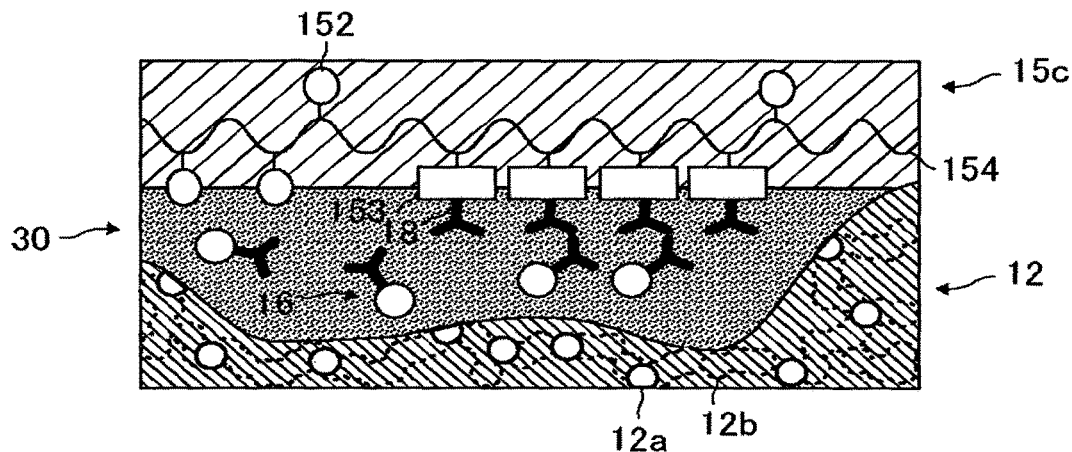
FIG. 5A is a cross-sectional diagram of a testing device, showing a portion at which a flow path member and a resin layer face each other.
Figure 5B:
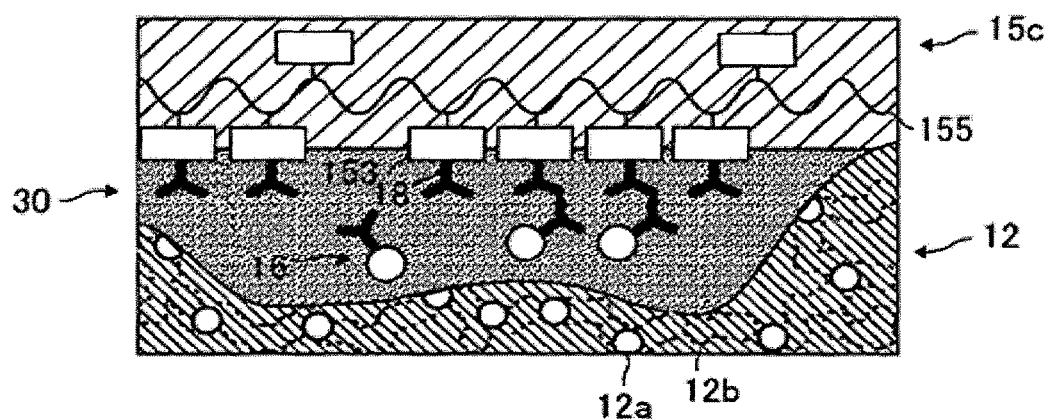
FIG. 5B is a cross-sectional diagram of a testing device, showing a portion at which a flow path member and a resin layer face each other.

First, an overall configuration of an embodiment will be described with reference to FIG. 1 to FIG. 5. FIG. 1 is a top plan view of a testing device according to an embodiment of the present invention. FIG. 2 is a cross-sectional diagram of the testing device of FIG. 1 taken along a line A-A. FIG. 3 is a cross-sectional diagram of the testing device, showing a portion at which a flow path member and a resin layer face each other. FIG. 4A and FIG. 4B are cross-sectional diagrams of the testing device, showing a portion at which a flow path member and a resin layer face each other. FIG. 5A and FIG. 5B are cross-sectional diagrams of the testing device, showing a portion at which a flow path member and a resin layer face each other.

The testing device 10 of FIG. 1 to FIG. 5 includes: a porous flow path member 12 in which there is formed a flow path for flowing a hydrophilic test liquid 30 (an example of a sample) such as blood, spinal fluid, urine, and a sample extraction liquid (i.e., a liquid containing a sample picked with a sample picking member such as a stick); and resin layers (15a, 15b, and 15c) provided over the flow path member 12. A labeled antibody 16, a capture antibody 17, and a capture antibody 18 (each being an example of a reagent) that are reactive with an antigen contained in the test liquid 30 are provided as a solid phase over surfaces of the resin layers (15a, 15b, and 15c) facing the flow path member 12, respectively. This makes it possible for the strength of the interaction between the resin layers (15a, 15b, and 15c) and the reagents to be adjusted on the basis of each independent resin layer (15a, 15b, and 15c). Therefore, even when the flow path member 12 is selected arbitrarily depending on the purpose, it is easy to control release and fixing of the reagents.

The present embodiment of the testing device 10 to be described below is a case where the flow path member 12 is provided over a base material 11, and an absorbent member 14 is provided over the base material 11 and the flow path member 12. However, the present invention is not limited to such an embodiment. In the present embodiment, what is meant when it is said that something is provided over a member is that that something is provided to have contact with that member, regardless of on which side of the testing device 10 it is when the testing device 10 is set in place. When an arbitrary resin layer among the resin layers (15a, 15b, and 15c) is to be mentioned, it will be denoted as resin layer 15. The reagents may be provided as a solid phase by means of any arbitrary interaction such as an arbitrary chemical bonding such as covalent bonding, hydrogen bonding, and metal bonding, attachment, adhesion, adsorption, and van der Waals binding.

The subsequent description will be about a case where the test liquid 30 is a hydrophilic test liquid such as blood, spinal fluid, urine, and a sample extraction liquid (a liquid containing a sample picked with a sample picking member such as a stick). As shown in FIG. 3, in the testing device 10, the resin layer 15a (second resin layer) contains an amphiphilic resin 151 (second amphiphilic resin) having many hydrophilic groups 152, and it is preferable that the resin layer 15a contain the amphiphilic resin 151 as a main component (i.e., in an amount of 50% by mass or higher). Hydrophilic groups mean a group of atoms that form a weak bond with water molecules via hydrogen bonding or the like and have affinity with water, and amphiphilicity means affinity with both of water and an organic solvent. The labeled antibody 16 has a hydrophilic portion 16g, and by means of this portion, is provided as a solid phase over the surface of the resin layer 15a facing the flow path member 12. Meanwhile, when the gap formed at the portion at which the flow path member 12 and the resin layer 15a face each other is filled with the test liquid 30, the hydrophilic portion 16g of the labeled antibody 16 becomes affinitive with the hydrophilic test liquid 30, and the labeled antibody 16 is released from the amphiphilic resin 151. When the test liquid contains an antigen 31, the released labeled antibody 16 and the antigen 31 react and conjugate with each other through an antigen-antibody reaction. In order to prevent inhibition of the conjugation between the antigen and the antibody, it is preferable that the amphiphilic resin 151 be a water-insoluble resin. In the present embodiment, water-insolubility means substantial insolubility to water. Here, a resin is defined as water-insoluble when the resin is immersed in a large amount of water at 25° C. for 24 hours, and then dried sufficiently by vacuum drying or the like, and as a result, has undergone weight change of 1% by mass or less. This is because a by-product (e.g., a monomer component) contained in the resin product may dissolve in the water and reduce the weight.

As shown in FIG. 4A and FIG. 4B, in the testing device 10, it is preferable that the resin layer 15b (first resin layer) be a resin having hydrophobic groups 153. Specifically, the resin layer 15b contains a hydrophobic resin 155 or an amphiphilic resin 154 (first amphiphilic resin) that has many hydrophobic groups 153, and it is preferable that the resin layer 15b contain the hydrophobic resin 155 or the amphiphilic resin 154 as a main component (i.e., in an amount of 50% by mass or higher). Hydrophobic groups mean a group of atoms that tend to repel water, have a low affinity with water, and cannot easily dissolve in water or mix with water. The capture antibody 17 has a hydrophobic portion 17g. The capture antibody 17 is provided as a solid phase over the surface of the resin layer 15b facing the flow path member 12, by this hydrophobic portion binding with the surface by means of an intermolecular force. When the gap formed at the portion at which the flow path member 12 and the resin layer 15b face each other is filled with the test liquid 30, the capture antibody 17 captures the antigen 31 in the state of being conjugated with the labeled antibody 16. As a result, the antigen 31 and the labeled antibody 16 are fixed and develop a color. Therefore, the resin layer 15b can be used as a test line for determination of presence or absence of the antigen 31. In order to prevent bleeding of the test line, it is preferable that the hydrophobic resin 155 and the amphiphilic resin 154 each be a water-insoluble resin.

As shown in FIG. 5A and FIG. 5B, in the testing device 10, the resin layer 15c (first resin layer) contains a hydrophobic resin 155 or an amphiphilic resin 154 that has many hydrophobic groups 153, and it is preferable that the resin layer 15c contain the hydrophobic resin 155 or the amphiphilic resin 154 as a main component (i.e., in an amount of 50% by mass or higher). The capture antibody 18 is provided as a solid phase over the surface of the resin layer 15c facing the flow path member 12, by the hydrophobic portion of the capture antibody 18 binding with the surface by means of an intermolecular force. The capture antibody 18 is not particularly limited, except that it should be able to capture the labeled antibody 16. Examples thereof include an antibody that specifically binds with the labeled antibody 16. As a result, the labeled antibody 16 is fixed and develops a color. Therefore, the resin layer 15c can be used as a control line for indicating that the labeled antibody 16 has reached. In order to prevent bleeding of the control line, it is preferable that the hydrophobic resin 155 and the amphiphilic resin 154 each be a water-insoluble resin.

It is preferable that the resin layers be a non-porous member. The non-porous member means a non-porous structure that contains substantially no voids and contrasts with a porous material such as a membrane that contains voids and is provided for promoting absorption of a liquid. Hence, for example, any structure that contains a few cells that have been mixed in the structure in the production process accidentally and would not contribute to promoting a liquid absorption action is encompassed within the category of the non-porous member.

Next, characteristics of the present invention that are attributed to the resin layers being a non-porous member will be described.

Conventionally, a test line and a control line have been formed by directly applying a liquid in which a capture antibody is dissolved over a flow path member made of a hydrophilic porous material. Therefore, the capture antibody is diffused through the porous material as a liquid permeates therethrough. However, colorant from labeling particles such as gold colloid particles that are bound with the capture antibody present in the porous material cannot be sensed actually, because light scattering occurs. That is, much of the capture antibody is not utilized effectively.

It is generally believed that colorant particles that can be sensed from within a porous material are those that are present by the depth of about 5 μm. In order to fix the capture antibody necessary for testing in the region present by the depth of 5 μm, it is necessary to apply a large amount of the capture antibody, taking into account diffusion in the direction of thickness. That is, the amount of the capture antibody to be applied increases in proportion to the thickness of the porous material.

On the other hand, according to the present invention, the capture antibody is fixed by means of the resin layers made of a non-porous member having many hydrophobic groups. Therefore, the capture antibody would not be mixed into the resin layers, but be fixed only on the surface of the resin layers. A color is developed by the capture antibody fixed over the surface of the resin layers being bound with labeling particles. The color can be sensed because sensing is through the resin layers made of the non-porous member that does not scatter light. Hence, the efficiency of utilization of color development by the labeling particles can be improved significantly. Because there are no extra colorant particles present in the direction of thickness, there is a merit that the amount of the capture antibody to be applied is very low. For example, it is assumed that when the thickness of a flow path member made of a hydrophilic porous material is 100 μm, it is only possible to utilize color development from a region present by a thickness of 5 μm from the surface. In this case, according to the present invention, it is possible to save the amount of the capture antibody to be used for obtaining color development that has the same intensity as in the above assumption to $1/20$.

Hence, according to the present invention, it is possible to improve the efficiency of utilization of color development by the labeling particles significantly because resin layers made of a non-porous member having many hydrophobic groups are used for fixing the capture antibody, and it is possible to reduce the amount of the capture antibody to be applied from conventional cases because there are no extra colorant particles present in the direction of thickness.

In the present embodiment, the testing device 10 for testing presence or absence of an antigen 31 in the test liquid 30 is described. However, the testing device of the present invention is not limited to one that utilizes an antigen-antibody reaction. For example, the testing device may be configured to test a specific component contained in the test liquid 30, by using as a reagent, one that changes its hue upon a structural change.

<<<Configuration of Each Member>>>

Each member of the testing device 10 described above will be described below in detail.

<<Base Material>>

In an embodiment of the present invention, the base material 11 is not particularly limited, and an arbitrary base material may be selected according to the purpose. Examples thereof include organic, inorganic, and metallic base materials. It is preferable that at least one surface of the base material 11 be coated with a hydrophobic resin, although this is not limiting. When the testing device 10 is used as a sensor chip, it is preferable to use a light, flexible, and low-cost synthetic resin as the base material 11. Further, according to the present embodiment, it is possible to select a highly durable base material 11 such as a plastic sheet, which consequently improves the durability of the testing device 10.

Examples of the base material 11 include base materials made of polyvinyl chloride, polyethylene terephthalate, polypropylene, polystyrene, polyvinyl acetate, polycarbonate, polyacetal, modified polyphenylether, polybutylene phthalate, and an ABS resin. Among these, it is particularly preferable to use a base material 11 made of polyethylene terephthalate a, because it is low-cost and highly versatile.

The shape of the base material 11 is not particularly limited, but is preferably a sheet shape. The average thickness of the base material 11 is not particularly limited, and may be appropriately selected according to the purpose. However, it is preferably from 0.01 mm to 0.5 mm. When the average thickness is less than 0.01 mm, the base material 11 may not be able to maintain strength to qualify as a base material. When the average thickness is greater than 0.5 mm, the base material may have a poor flexibility depending on the material thereof, and may lack a handling easiness as a sensor. In the present embodiment, an average thickness may be an average of thicknesses measured with a micrometer at a total of 15 positions of the measurement target, namely 5 positions in the longer direction and 3 positions in the width direction that are at substantially equal intervals. In the present embodiment, a thickness can be defined as a length of a measurement target in a direction perpendicular to an interface at which the base material 11 and the flow path member 12 contact each other.

<<Flow Path Member>>

The flow path member 12 of the testing device 10 is not particularly limited, except that it should be able to flow the test liquid 30 therethrough. Examples thereof include a hydrophilic porous material. The flow path member 12 made of a hydrophilic porous material includes voids (12a and 12b), and a flow path is formed when the test liquid 30 flows through the voids (12a and 12b). In FIG. 3 to FIG. 5, the voids 12a are voids formed in the respective cross-sections, and the voids 12b are voids in a deeper portion in the cross-sections. It is preferable that cells be present in the hydrophilic porous material, and that the cells be linked and form a continuous cell. A continuous cell is different from independent cells that are not linked. The cells forming a continuous cell have a minute pore in the wall between the cells. Therefore, the continuous cell has a function of absorbing a liquid by means of a capillary action or letting a gas pass through. The flow path member 12 delivers the test liquid 30 by utilizing a capillary action through the voids (12a and 12b). Therefore, an external actuator such as a pump is unnecessary.

The hydrophilic porous material is not particularly limited, and an arbitrary hydrophilic porous material may be selected according to the purpose. However, it is preferably a base material having hydrophilicity and a high voidage. A hydrophilic porous material is a porous material that is easily permeable by an aqueous solution. A material can be said to be easily permeable, when in a test for water permeability evaluation, a plate-shaped test piece of the material is dried for 1 hour at 120° C., pure water (0.01 mL) is dropped down onto the surface of the dried test piece, and the pure water (0.01 mL) completely permeates the test piece within 10 minutes.

The voidage of the hydrophilic porous material is not particularly limited, and may be appropriately selected according to the purpose. However, it is preferably from 40% to 90%, and more preferably from 65% to 80%. When the voidage is greater than 90%, the hydrophilic porous material may not be able to keep the strength to qualify as a base material. When the voidage is less than 40%, the permeability of the test liquid 30 may be poor. The voidage can be calculated according to the calculation formula 1 below, based on the basis weight (g/m$^2$) and the thickness (μm) of the hydrophilic porous material, and the specific gravity of the component thereof.

Voidage (%)={1−[basis weight (g/m$^2$)/thickness (μm)/specific gravity of the component]}×100     [Calculation Formula 1]

The hydrophilic porous material is not particularly limited, and an arbitrary hydrophilic porous material may be selected according to the purpose. Examples thereof include filter paper, regular paper, high-quality paper, watercolor paper, Kent paper, synthetic paper, synthetic resin film, special-purpose paper having a coating layer, fabric, fiber product, film, inorganic substrate, and glass.

Examples of the fabric include artificial fiber such as rayon, bemberg, acetate, nylon, polyester, and vinylon, natural fiber such as cotton and silk, blended fabric of those above, or non-woven fabric of those above.

Among these, filter paper is preferable because it has a high voidage and a favorable hydrophilicity. When the testing device 10 is used as a biosensor, the filter paper is preferable as the stationary phase of the paper chromatography.

The shape of the hydrophilic porous material is not particularly limited and may be appropriately selected according to the purpose. However, the hydrophilic porous material is preferably a sheet-shaped. The average thickness of the hydrophilic porous material is not particularly limited and may be appropriately selected according to the purpose. However, it is preferably from 0.01 mm to 0.3 mm. When the average thickness is less than 0.01 mm, the hydrophilic porous material may not be able to keep the strength to qualify as a base material. When the average thickness is greater than 0.3 mm, a requisite amount of the test liquid 30 may be high.

<<Resin Layer>>

Figure 6:
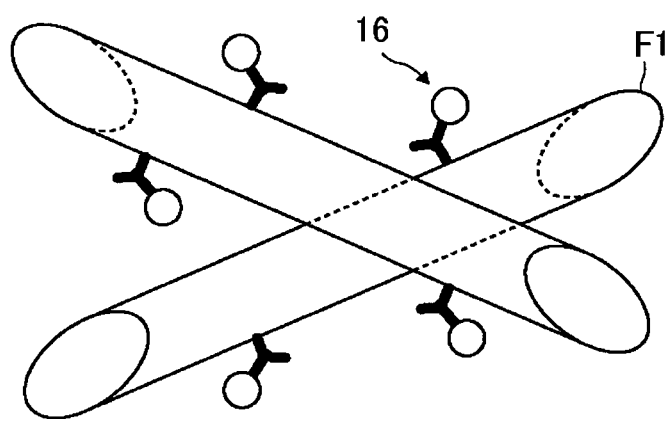
FIG. 6 is a conceptual diagram of a conjugate pad of a conventional testing device.
Figure 7:
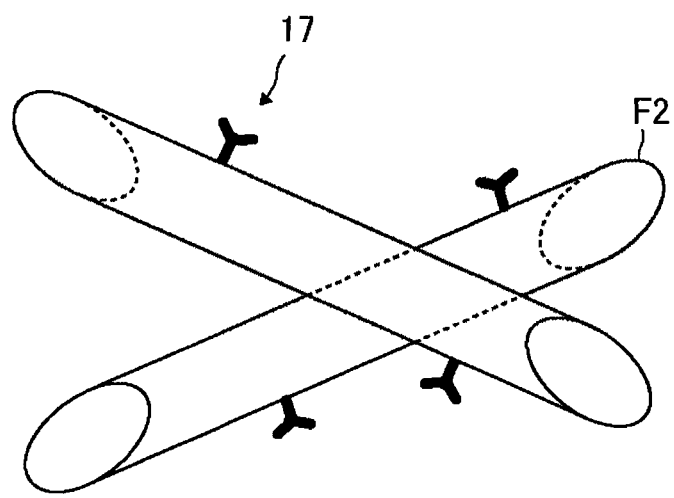
FIG. 7 is a conceptual diagram of a membrane of a conventional testing device.

First, a function of the resin layer 15 will be described in comparison with a conventional testing device shown in FIG. 6 and FIG. 7. FIG. 6 is a conceptual diagram of a conjugate pad of a conventional testing device. FIG. 7 is a conceptual diagram of a membrane of a conventional testing device. It has been often the case with a conventional testing device that when the conjugate pad has an excessively high hydrophilicity, the conjugate pad tends to retain the test liquid therein and cannot flow it to the membrane smoothly. On the other hand, when the conjugate pad has an excessively high hydrophobicity, the conjugate pad can flow the test liquid to the membrane smoothly, but has a poor absorptivity of the test liquid from the sample pad, which has been the cause of a long testing time and a high requisite amount of the test liquid. Therefore, there have been limitations to fibers F1 that can be used as a conjugate pad. Furthermore, in the conventional testing device, the labeled antibody 16 is provided as a solid phase over the fiber F1 constituting the conjugate pad (see FIG. 6). Therefore, labeled antibodies 16 that can be released from the conjugate pad are only those that have a weak binding with the fiber F1. That is, fibers F1 and labeled antibodies 16 that can be used in the conventional testing device are limited in terms of design.

Likewise, in a conventional testing device, the capture antibody 17 is provided as a solid phase over a fiber F2 constituting the membrane (see FIG. 7). Therefore, capture antibodies 17 that can be fixed on the membrane are only those that have a strong binding with the fiber F2. That is, fibers F2 and capture antibodies 17 that can be used in the conventional testing device are limited in terms of design.

Meanwhile, in the testing device 10 of the present embodiment, the reagents such as the labeled antibody 16, the capture antibody 17, and the capture antibody 18 are provided as a solid phase over resin layers (15a, 15b, and 15c). Therefore, it is possible to control release or fixing of the reagents depending on the strength of interaction between the resin layers 15 and the reagents and affinity of the resin layers with the test liquid 30. The method for adjusting the strength of interaction and affinity may be a method of changing the kind or the composition ratio of the resin constituting the resin layers 15 depending on the corresponding reagents. For example, the higher a hydrophobic percentage is in the resin constituting the resin layers 15, the easier it is for the resin layers 15 to have a reagent having a hydrophobic group fixed thereon by means of a hydrophobic interaction. Here, a hydrophobic interaction means a cause (driving force) of a change occurring in water that hydrophobic molecules or hydrophobic groups that repel water coalesce with each other. More specifically, in many cases when hydrophobic molecules or molecules having a hydrophobic group are added in water, not only do they not dissolve in water, but the hydrophobic molecules and hydrophobic groups come into contact with each other and try as hard as possible to reduce the contact area with the water molecules. As a result, the hydrophobic molecular species coalesce with each other, and appear to have a binding force between the molecules. This phenomenon is called a hydrophobic interaction. On the other hand, when a hydrophilic percentage is high in the resin constituting the resin layers 15, it is estimated that although the resin layers 15 have a strong interaction with a hydrophilic reagent, the reagent becomes affinitive with the test liquid 30 and is easily released into the test liquid 30 when the binding portion comes into contact with the hydrophilic test liquid 30.

It is preferable that the resin constituting the resin layers 15 be a water-insoluble resin. A water-insoluble resin can avoid dissolving in the test liquid 30, and hence prevent clogging the flow path or smudging a control line or a test line. Examples of the amphiphilic resin of which the resin layer 15a is mainly composed include polyvinyl alcohols, a polyvinyl acetal resin, polyacrylic acid, an acrylic acid/ acrylonitrile copolymer, a vinyl acetate/acrylic ester copolymer, an acrylic acid/acrylic ester copolymer, a styrene/ acrylic acid copolymer, a styrene/methacrylic acid copolymer, a styrene/methacrylic acid/acrylic ester copolymer, a styrene/α-methyl styrene/acrylic acid copolymer, a styrene/α-methyl styrene/acrylic acid/acrylic ester copolymer, a styrene/maleic acid copolymer, a styrene/maleic anhydride copolymer, a vinylnaphthalene/acrylic acid copolymer, a vinylnaphthalene/maleic acid copolymer, a vinyl acetate/maleic ester copolymer, a vinyl acetate/crotonic acid copolymer, a vinyl acetate/acrylic acid copolymer, and a salt of these. One of these may be used alone, or two or more of these may be used in combination.

Among these, a copolymer of a monomer having a hydrophobic functional group and a monomer having a hydrophilic functional group, and a polymer produced from a monomer having both of a hydrophobic functional group and a hydrophilic functional group are preferable. In terms of a morphic property, the copolymer may be any of a random copolymer, a block copolymer, an alternate copolymer, and a graft copolymer.

Examples of the hydrophobic resin of which the resin layers 15b and 15c are mainly composed include: a polystyrene-based resin such as polystyrene, and an acrylonitrile/ butadiene/styrene-based resin; a polyolefin-based resin or a cyclic polyolefin-based resin such as a polypropylene resin, a polyethylene resin, and an ethylene/propylene copolymer; a methacryl-based resin such as a polycarbonate resin, a polyethylene terephthalate resin, and a polymethyl methacrylate resin; a fluorine-based resin such as a vinyl chloride resin, a polybutylene terephthalate resin, a polyarylate resin, a polysulfone resin, a polyether sulfone resin, a polyether ether ketone resin, a polyether imide resin, and a polytetrafluoroethylene resin; an acrylic-based resin such as a polymethyl pentene resin, and polyacrylonitrile; and a cellulose-based resin such as a propionate resin. Other examples include natural wax such as beeswax, carnauba wax, spermaceti, Japan tallow, candelilla wax, rice wax, and montan wax; synthetic wax such as paraffin wax, microcrystalline wax, oxide wax, ozokerite, ceresin, ester wax, polyethylene wax, and polyethylene oxide wax; higher fatty acid such as margaric acid, lauric acid, myristic acid, palmitic acid, stearic acid, furoic acid, and behenic acid; higher alcohol such as stearin alcohol and behenyl alcohol; esters such as sorbitan fatty acid ester; and amides such as stearamide and oleic amide. One of these may be used alone or two or more of these may be used in combination. Among these, polystyrene resin, polyolefin resin, carnauba wax, and polyethylene wax are preferable because they have a strong hydrophobic interaction.

It is possible to use the same kind of a resin as the resin for constituting the respective resin layers (15a, 15b, and 15c). In this case, it is preferable that the resin constituting the resin layer 15a have a greater degree of hydrophilicity than that of the resin constituting the resin layers (15b and 15c). When the same kind of a resin is used, it is not indispensable to measure the hydrophilicity to say that one resin layer has a greater degree of hydrophilicity, as long as, it contains a greater percentage of hydrophilic groups.

The labeled antibody 16 provided as a solid phase over the resin layer 15a is not particularly limited, except that it should have a hydrophilic portion and be able to react with the antigen 31. Examples thereof include a gold colloid-labeled antibody such as gold colloid-labeled anti-human IgG, and labeled antibody against various allergens. Particles for labeling the antibody are not particularly limited to gold colloid, and other examples include colloid of any other metal, enzyme labeling particles containing an enzyme, coloring particles containing a pigment, fluorescent particles containing a fluorescent substance, and magnetic body-capsulating particles containing a magnetic body. The capture antibody 17 provided as a solid phase over the resin layer 15b is not particularly limited except that it should have a hydrophobic portion and be able to react with the antigen 31. Examples thereof include anti-human IgG, and antibodies against various allergens. The antibody may be a monoclonal antibody, a polyclonal antibody, a chimeric antibody, a Fab antibody, and a (Fab)2 antibody. The antibody 18 provided as a solid phase over the resin layer 15c is not particularly limited except that it should have a hydrophobic group and be able to react with the labeled antibody 16. Examples thereof include an antibody against the labeled antibody 16, such as Human IgG. Other examples thereof include the antibodies given above.

The method for providing the reagents such as the labeled antibody 16 and the capture antibodies (17 and 18) over the resin layers 15 is not particularly limited, and may be a method of applying a solution containing the reagents over the resin layers 15 and then fast-drying the solution, or a method of applying a solution containing the reagents over the resin layers 15, keeping the solution-applied resin layers stationary under a humid atmosphere so as not for the applied solution to dry, washing the surface of the resin layers as lightly as rinsing with a liquid containing the same components as the aqueous solution in which the reagents are dissolved, and then drying the surface.

In the present embodiment, it is preferable that the resin layers 15 be fixed over the flow path member 12. The method for fixing the resin layers 15 is not particularly limited, except that the resin layers should be fixed such that the reagents and the test liquid 30 can contact each other during a test. Specific examples of the method include a method of thermally transferring the resin to constitute the resin layers onto the flow path member 12 with a thermal transfer printer or the like, a method of transferring the resin to constitute the resin layers by applying a pressure thereto with a dot impact printer or the like, and a method of sticking the resin to constitute the resin layers to the flow path member 12 with a tape, an adhesive, a gluing agent, or the like.

<<Absorbent Member>>

The absorbent member 14 is not particularly limited, and any absorbent member may be selected from publicly-known materials as long as it is water-absorptive. Examples of the absorbent member 14 include paper, a fiber such as cloth, a high-molecular compound having a carboxyl group or a salt thereof, a partially cross-linked product of a high-molecular compound having a carboxyl group or a salt thereof, and a partially cross-linked product of a polysaccharide.

<<Transfer Member>>

As described above, the resin layers 15 may be provided over the flow path member 12 by various methods. As an example, a case of using a thermal transfer method will be described below. A transfer member for fabrication of the testing device 10 and a transfer method, which are used in a thermal transfer method, will be described below.

Figure 8:
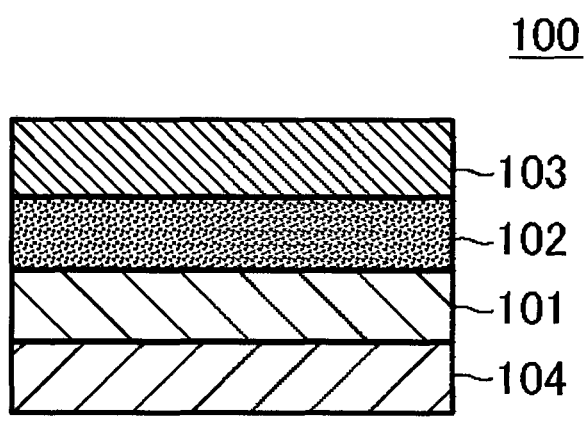
FIG. 8 is a cross-sectional diagram of a transfer member according to an embodiment of the present invention.

With reference to FIG. 8, a reagent transfer member used for forming the resin layer 15 over the flow path member 12 will be described. FIG. 8 is a cross-sectional diagram of a reagent transfer member according to an embodiment of the present invention. In the case of using a thermal transfer method, it is possible to use a transfer member that is previously coated with a reagent uniformly. Therefore, it is possible to suppress the capture antibodies (17 and 18) from being varied in concentration along a test line or a control line. Further, in the case of placing a capture antibody by a conventional application method, it is necessary to dilute the capture antibody with a solvent until it reaches an applicable viscosity (e.g., until it becomes dischargeable from an inkjet printer). However, in the case of placing a capture antibody by thermal transfer, use of a transfer member that is previously coated with a reagent at a high concentration makes it possible to place the capture antibody in the flow path at a high concentration.

A reagent transfer member 100 (an example of a transfer member) includes a support member 101, a release layer 102 provided over the support member 101, and a solid reagent phase layer 103 provided over the release layer 102. A reagent is provided as a solid phase over a surface of the solid reagent phase layer 103. The reagent transfer member 100 further includes other layers such as a back layer 104 according to necessity.

—Support Member—

The shape, structure, size, material, etc. of the support member 101 are not particularly limited, and may be appropriately selected according to the purpose. The structure may be a single-layered structure, or a multilayered structure. The size of the support member may be appropriately selected according to the size of the testing device 10, etc.

The material of the support member 101 is not particularly limited, and may be appropriately selected according to the purpose. Examples thereof include: polyester such as polyethylene terephthalate (PET), and polyethylene naphthalate (PEN); polycarbonate; a polyimide resin (PI); polyamide; polyethylene; polypropylene; polyvinyl chloride; polyvinylidene chloride; polystyrene; a styrene/acrylonitrile copolymer; and cellulose acetate. One of these may be used alone, or two or more of these may be used in combination. Among these, polyethylene terephthalate (PET), and polyethylene naphthalate (PEN) are particularly preferable.

It is preferable to apply a surface activation treatment to a surface of the support member 101 in order to impart a better close adhesiveness with a layer to be provided over the support member 101. Examples of the surface activation treatment include a glow discharge treatment and a corona discharge treatment.

After the solid reagent phase layer 103 is transferred onto the hydrophilic porous material, the support member 101 may be kept there. Alternatively, after the solid reagent phase layer 103 is transferred, the support member 101 may be peeled and removed by means of the release layer 102. The support member 101 is not particularly limited, and may be an appropriately synthesized product or a commercially available product. The average thickness of the support member 101 is not particularly limited, and may be appropriately selected according to the purpose. However, it is preferably from 3 µm to 50 µm.

—Release Layer—

The release layer 102 has a function of improving separability between the support member 101 and the solid reagent phase layer 103 during transfer. The release layer 102 also has a function of thermally melting to a low viscosity liquid when heated with a heating/pressurizing unit such as a thermal head to thereby make it easier for the solid reagent phase layer 103 to be separated at the interface between the heated portion and a non-heated portion. The release layer 102 contains a wax and a binder resin, and further contains other components appropriately selected according to necessity.

The wax is not particularly limited, and an appropriate wax may be selected according to the purpose. Examples thereof include: natural wax such as beeswax, carnauba wax, spermaceti, Japan tallow, candelilla wax, rice wax, and montan wax; synthetic wax such as paraffin wax, microcrystalline wax, oxide wax, ozokerite, ceresin, ester wax, polyethylene wax, and polyethylene oxide wax; higher fatty acid such as margaric acid, lauric acid, myristic acid, palmitic acid, stearic acid, furoic acid, and behenic acid; higher alcohol such as stearin alcohol and behenyl alcohol; esters such as sorbitan fatty acid ester; and amides such as stearamide and oleic amide. One of these may be used alone or two or more of these may be used in combination. Among these, carnauba wax and polyethylene wax are preferable because they are excellent in releasability.

The binder resin is not particularly limited, and appropriate binder resin may be selected according to the purpose. Examples thereof include an ethylene/vinyl acetate copolymer, a partially saponified ethylene/vinyl acetate copolymer, an ethylene/vinyl alcohol copolymer, an ethylene/sodium methacrylate copolymer, polyamide, polyester, polyurethane, polyvinyl alcohol, methyl cellulose, carboxymethyl cellulose, starch, polyacrylic acid, an isobutylene/maleic acid copolymer, a styrene/maleic acid copolymer, polyacrylamide, polyvinyl acetal, polyvinyl chloride, polyvinylidene chloride, an isoprene rubber, a styrene/butadiene copolymer, an ethylene/propylene copolymer, a butyl rubber, and an acrylonitrile/butadiene copolymer. One of these may be used alone, or two or more of these may be used in combination.

The method for forming the release layer 102 is not particularly limited, and an appropriate method may be selected according to the purpose. Examples thereof include a hot-melt coating method, and a coating method using a coating liquid obtained by dispersing the wax and the binder resin in a solvent. The average thickness of the release layer 102 is not particularly limited and may be appropriately selected according to the purpose. However, it is preferably from 0.5 µm to 50 µm. The amount of deposition of the release layer 102 is not particularly limited and may be appropriately selected according to the purpose. However, it is preferably from 0.5 g/m$^2$ to 50 g/m$^2$.

—Solid Reagent Phase Layer—

The solid reagent phase layer 103 needs only to contain a resin to constitute the resin layers 15 of the testing device 10, and the material thereof is not limited. The method for forming the solid reagent phase layer 103 is not particularly limited, and an appropriate method may be selected according to the purpose. For example, as a hot-melt coating method or a coating method using a reagent coating liquid obtained by dispersing the resin to constitute the resin layers 15 in a solvent, a common coating method using a gravure coater, a wire bar coater, a roll coater, or the like may be used. According to such a method, the support member 101 or the release layer 102 is coated with the solid reagent phase layer coating liquid. When the liquid is dried, the solid reagent phase layer is formed.

The average thickness of the solid reagent phase layer 103 is not particularly limited and may be appropriately selected according to the purpose. However, it is preferably from 200 nm to 50 μm. When the average thickness is less than 200 nm, the resin layer may have a poor durability and be broken by friction or an impact. When the average thickness is greater than 50 μm, it becomes harder for heat from the thermal head to be conducted uniformly through the solid reagent phase layer, to thereby degrade sharpness.

The amount of deposition of the reagent coating liquid in the solid reagent phase layer 103 is not particularly limited, and may be appropriately selected according to the purpose. However, it is preferably from 0.2 $g/m^2$ to 50 $g/m^2$. When the amount of deposition is less than 0.2 $g/m^2$, the coating amount may be insufficient, and the resin layers may have deficits. When the amount of deposition is greater than 50 $g/m^2$, it may take time to dry the liquid, or the resin layers may have unevenness.

After the reagent coating liquid is dried and the solid reagent phase layer 103 is formed, it is possible to form the labeled antibody 16 or the capture antibody (17 or 18) as a solid phase over the surface of the solid reagent phase layer 103, by applying a solution containing the labeled antibody 16 or the capture antibody (17 or 18) over the surface of the solid reagent phase layer 103 to form a uniform coating film, and then drying the coating film. It is preferable that the coating film be applied to have a uniform thickness. The drying method is not particularly limited and may be through-flow drying, vacuum drying, natural drying, freeze drying, etc. However, it is preferable to dry the coating film at reduced pressure or in a vacuum. The drying temperature is preferably room temperature of from 20° C. to 50° C., and the drying time is preferably from 30 minutes to 24 hours. When the drying temperature is lower than 20° C., it takes a longer time to dry, which may reduce the productivity. When the drying temperature is higher than 50° C., the reagent may be degenerated. When the drying time is shorter than 30 minutes, the coating film may be dried insufficiently. When the drying time is longer than 24 hours, the productivity may be low, and the color of the resin may be changed depending on the kind of the resin.

After the reagent coating liquid is dried and the solid reagent phase layer 103 is formed, it is also possible to form the labeled antibody 16 or the capture antibody (17 or 18) as a solid phase, by applying a solution containing the labeled antibody 16 or the capture antibody (17 or 18) over the surface of the solid reagent phase layer 103, keeping the solution-applied solid reagent phase layer 103 stationary under a humid atmosphere so as not for the applied solution to dry, washing the surface of the resin layer as lightly as rinsing with a liquid containing the same components as the aqueous solution in which the reagents are dissolved, and then drying the surface. Preferable ranges of the drying conditions (drying time, drying temperature) are as described above.

—Back Layer—

It is preferable that the reagent transfer member 100 include a back layer 104 over a surface of the support member 101 opposite to a surface thereof over which the release layer 102 is provided. During transfer, heat is directly applied by a thermal head or the like to this opposite surface in a manner to match the shape of the resin layers. Therefore, it is preferable that the back layer 104 have resistance to high heat, and resistance to friction with the thermal head or the like. The back layer 104 contains a binder resin, and further contains other components according to necessity.

The binder resin is not particularly limited, and an arbitrary binder resin may be selected according to the purpose. Examples thereof include a silicone-modified urethane resin, a silicone-modified acrylic resin, a silicone resin, a silicone rubber, a fluorine resin, a polyimide resin, an epoxy resin, a phenol resin, a melamine resin, and nitrocellulose. One of these may be used alone, or two or more of these may be used in combination.

The other components are not particularly limited, and arbitrary components may be selected according to the purpose. Examples thereof include inorganic particles such as talc, silica, and organopolysiloxane, and a lubricant.

The method for forming the back layer 104 is not particularly limited, and an arbitrary method may be selected according to the purpose. Examples thereof include a common coating method using a gravure coater, a wire bar coater, a roll coater, etc. The average thickness of the back layer 104 is not particularly limited, and may be appropriately selected according to the purpose. However, it is preferably from 0.01 μm to 1.0 μm.

—Undercoat Layer—

It is possible to provide an undercoat layer between the support member 101 and the release layer 102, or between the release layer 102 and the solid reagent phase layer 103. The undercoat layer contains a resin, and further contains other components according to necessity. The resin is not particularly limited, and an arbitrary resin may be selected according to the purpose. The various kinds of resins usable as the solid reagent phase layer 103 and the release layer 102 can be used.

—Protective Film—

It is preferable to provide a protective film over the solid reagent phase layer 103 for protection from contamination or damages during storage. The material of the protective film is not particularly limited, and an arbitrary material may be selected according to the purpose as long as it can be peeled from the solid reagent phase layer 103 easily. Examples thereof include a silicone, sheet, a polyolefin sheet such as polypropylene sheet, and a polytetrafluoroethylene sheet. The average thickness of the protective film is not particularly limited, and may be appropriately selected according to the purpose. However, it is preferably from 5 μm to 100 μm, and more preferably from 10 μm to 30 μm.

<<Transfer of Solid Reagent Phase Layer>>

The method for thermally transferring the solid reagent phase layer 103 onto the flow path member 12 may be a method including a step of bringing the solid reagent phase layer 103 of the reagent transfer member 100 into contact with the flow path member 12, and transferring the solid reagent phase layer 103 onto the flow path member 12. A printer used for thermal transfer is not particularly limited, and an arbitrary printer may be selected according to the purpose. Examples thereof include a thermal printer including a serial thermal head, a line-shaped thermal head, or the like. The energy applied for thermal transfer is not particularly limited, and may be appropriately selected according to the purpose. However, it is preferably from 0.05 mJ/dot to 0.5 mJ/dot. When the applied energy is lower than 0.05 mJ/dot, the solid reagent phase layer 103 may be melted insufficiently. When the applied energy is higher than 0.5 mJ/dot, the reagent may be degenerated due to heat, or any portion of the reagent transfer member 100 other than the solid reagent phase layer 103 may be melted to contaminate the thermal head.

<<Application of Testing Device>>

Applications of the testing device 10 are not particularly limited, and arbitrary applications may be selected according to the purpose. Examples thereof include a biochemical sensor (sensing chip) for blood testing or DNA testing, and a compact analytical device (chemical sensor) for quality control of foods and beverages.

Samples used for testing in a biochemical field are not particularly limited, and arbitrary samples may be selected according to the purpose. Examples thereof include a pathogen such as a bacterium and a virus, blood, saliva, a lesional tissue, etc. separated from living organisms, and egestion such as enteruria. Further, for performing a prenatal diagnosis, the sample may be a part of a fetus cell in an amniotic fluid, or of a dividing egg cell in a test tube. Furthermore, these samples may be, after condensed to a sediment directly or by centrifugation or the like according to necessity, subjected to a pre-treatment for cell destruction through an enzymatic treatment, a thermal treatment, a surfactant treatment, and an ultrasonic treatment, any combinations of these, etc.

The testing device 10 of the present embodiment also has a function of performing chromatography (separation and refinement) of a test liquid, because the flow path member 12 serves as a stationary phase. In this case, the flow path member 12 containing a continuous cell of which internal wall has hydrophilicity serves as the stationary phase (a carrier). Different components in the test liquid flow through the flow path at different speeds because of difference in their interactions with the stationary phase during the process of their permeation through the fluid path, i.e., difference in whether they are hydrophilic or hydrophobic.

A component having a higher hydrophilicity is more likely to adsorb to the porous portion serving as the stationary phase, and repeats adsorbing and desorbing more times. Therefore, such a component permeates the fluid path at a lower speed. Conversely, a component having a higher hydrophobicity permeates without adsorbing to the stationary phase. Therefore, such a component moves rapidly through the fluid path. By utilizing the difference in the moving speed in the test liquid, and extracting the target component in the test liquid 30 selectively and allowing it to undergo a reaction, it is possible to use the testing device 10 as a highly functional chemical or biochemical sensor.

<<<Testing Method>>>

A testing method using the testing device 10 is not particularly limited, and may include a step of supplying a hydrophilic test liquid into the flow path member 12 of the testing device 10, and a step of bringing the labeled antibody 16 (an example of a reagent) formed as a solid phase over the resin layer 15a into contact with the test liquid 30 to thereby release the labeled antibody from the resin layer 15a. The testing method using the testing device 10 may include a step of supplying the test liquid 30 into the flow path member of the testing device 10, and a step of capturing an antigen 31 (an example of a portion of a sample) with the capture antibody 17 formed as a solid phase over the resin layer 15b, when any antigen 31 is contained in the test liquid 30.

In a specific process, the hydrophilic test liquid 30 is dropped and supplied into a dropping portion 12c (see FIG. 1) formed in the flow path member 12 of the testing device 10. Subsequently, the supplied test liquid 30 is brought into contact with the labeled antibody 16 formed as a solid phase over the resin layer 15a, so that the labeled antibody may be released from the resin layer 15a. When any antigen 31 is contained in the test liquid 30, the labeled antibody 16 released from the resin layer 15a reacts and conjugates with the antigen 31 (see FIG. 3).

Subsequently, the test liquid 30 containing the labeled antibody 16 and the antigen 31 spreads through the flow path member 12 and reaches a region where the resin layer 15b is provided. The capture antibody 17 formed as a solid phase over a surface of the resin layer 15 facing the flow path member 12 conjugates with and captures also the antigen 31 that is in a state of being conjugated with the labeled antibody 16. The capture antibody 17 is formed as a solid phase over the resin layer 15b by means of the hydrophobic group 17g. Therefore, even when it contacts the test liquid 30, it does not become affinitive with the test liquid 30 and is not easily released into the test liquid. Even if a portion of the capture antibody 17 is released into the test liquid 30, the released portion binds with a fiber constituting the flow path member 12 soon after. Hence, the labeled antibody 16 is fixed at just about the resin layer 15b, and hence the test line sharply develops a color (see FIG. 4A and FIG. 4B).

Any labeled antibody 16 that passes the resin layer 15b without being captured there spreads through the flow path member 12 and reaches a region where the resin layer 15c is provided. In the present embodiment, the capture antibody 18 having a hydrophobic group is formed as a solid phase over a surface of the resin layer 15c facing the flow path member 12. The labeled antibody 16 conjugates with the capture antibody 18 and is hence captured. The capture antibody 18 is formed as a solid phase over the resin layer 15c by means of a hydrophilic group. Therefore, even when it contacts the test liquid 30, it does not become affinitive with the test liquid 30 and is not easily released into the test liquid. Even if a portion of the capture antibody 18 is released into the test liquid 30, the released portion binds with a fiber constituting the flow path member 12 soon after. Hence, the labeled antibody 16 is fixed at just about the resin layer 15c, and hence the control line sharply develops a color (see FIG. 5A and FIG. 5B).

<<<Testing Kit>>>

Figure 9:
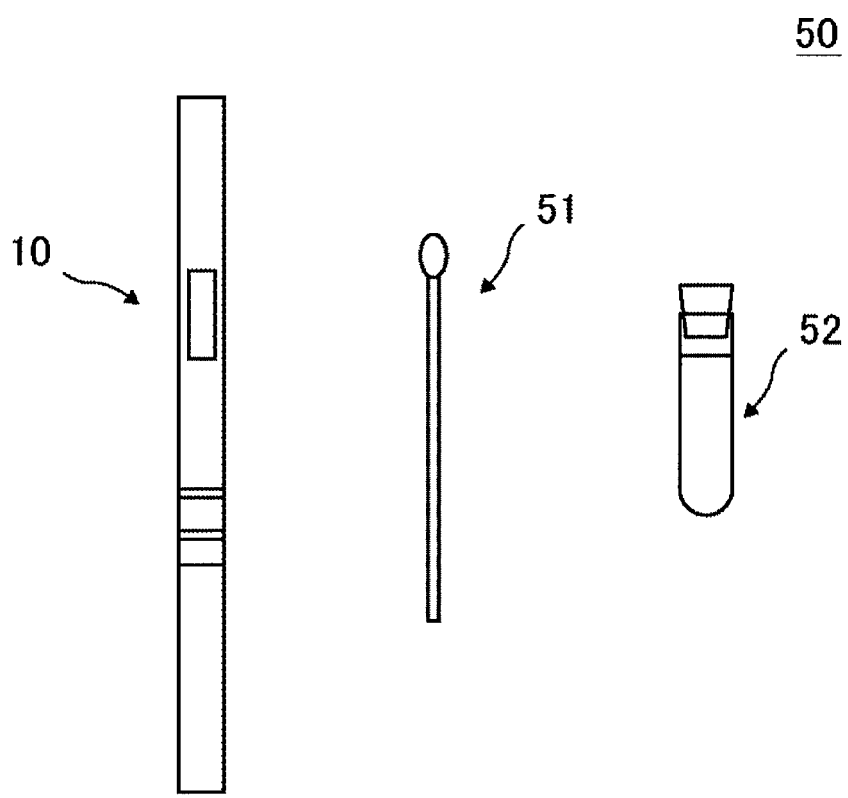
FIG. 9 is a conceptual diagram of a testing kit according to an embodiment of the present invention.

For performing a test according to the testing method described above, it is possible to use a testing kit that includes: the testing device 10; and a tool for picking a sample (an example of a sample picking member), or a liquid for treating a sample, or both thereof. FIG. 9 is a conceptual diagram of a testing kit according to an embodiment of the present invention. Examples of the tool for picking a sample include publicly-known tools such as a sterilized cotton swab 51 for picking a sample from throat, nasal cavity, or the like. Examples of the liquid for treating a sample include publicly-known liquids such as a dilution buffer 52 for diluting a sample, and an extractant liquid for extracting a sample.

<<<Supplemental to Embodiment>>>

The embodiment described above is about a case where the reagents formed as a solid phase over the resin layers 15 are an antigen or an antibody. However, the present invention is not limited to this embodiment. An indicator used in a chemical assay means a reagent that indicates a chemical property of a solvent. The indicator is not particularly limited, and examples thereof include a pH indicator, various ionophores that change colors by reacting with various ions such as a lead ion, a copper ion, and a nitrite ion, and reagents that change colors by reacting with various agricultural chemicals.

The embodiment described above is about a case where the support member 101 and the solid reagent phase layer 103 of the reagent transfer member 100 are separated from each other by heat during transfer. However, the present invention is not limited to this embodiment. For example, the support member 101 and the solid reagent phase layer 103 may be separated from each other by light. In this case, the release layer 102 may contain a light absorption agent such as carbon black, so that it may generate heat by absorbing light. In this way, the release layer 102 may be melted to let the solid reagent phase layer 103 be separated. Alternatively, the release layer 102 may contain a material that degenerates upon light irradiation. By making the material absorb light to make the release layer 102 fragile, it is possible to separate the solid reagent phase layer 103.

The embodiment described above is about a case where a flow path is formed throughout the flow path member 12. The present invention is not limited to this. As a method for forming a flow path in a partial portion of the flow path member 12, there is a method of forming a flow path wall that forms the outer contour of the flow path, by filling a hydrophobic material into voids of a hydrophilic porous material by a publicly-known method.

The testing device 10 of the present embodiment may be provided with an arbitrary protective member for the purposes of preventing contamination when a hand touches the flow path member 12. Examples of such a protective member include a housing that covers the entire testing device 10, and a film provided over the flow path member 12. When providing a protective member, it is preferable to form an opening at a portion thereof that is above the dropping portion 12c of the flow path member 12. It is also preferable to form an opening in the protective member for releasing pressure in the flow path.

The embodiment described above is about a case where the resin layers 15 are provided at a plurality of positions over the flow path member 12. However, depending on the kind of the reagent, there may be a resin layer 15 at only one position over the flow path member 12. For example, when the flow path member 12 that is provided with a resin layer 15a1 over which a reagent that specifically binds with a component A in the test liquid is formed as a solid phase, and resin layers 15b1 and 15c1 over which reagents for capturing them are formed as a solid phase is further provided with a resin layer 15a2 over which a reagent that specifically binds with a component B in the test liquid is formed as a solid phase, and resin layers 15b2 and 15c2 over which reagents for capturing them are formed as a solid phase, a testing device that can detect a plurality of components at the same time can be obtained.

The embodiment described above is about a case where the test liquid 30 is hydrophilic. However, the present invention is not limited to this embodiment. For example, the test liquid may be a solvophilic test liquid that contains an organic solvent such as alcohols (e.g., methyl alcohol, ethyl alcohol, 1-propyl alcohol, and 2-propyl alcohol), and ketones (e.g., acetone, and MEK (methyl ethyl ketone)). In this case, "hydrophilicity" in the embodiment described above should be replaced with "hydrophobicity", and "hydrophobicity" in the embodiment described above should be replaced with "hydrophilicity".

EXAMPLES

Examples of the present invention will be described below. However, the present invention is not limited to these Examples by any means.

Example 1

<<Production of Reagent Thermal Transfer Member>>
<Preparation of Solution>
1. Preparation of Back Layer Coating Liquid A silicone-based rubber emulsion (KS779H manufactured by Shin-Etsu Chemical Co., Ltd., with a solid content of 30% by mass) (16.8 parts by mass), a chloroplatinic acid catalyst (0.2 parts by mass), and toluene (83 parts by mass) were mixed, to thereby obtain a back layer coating liquid.

2. Preparation of Release Layer Coating Liquid

A polyethylene wax (POLYWAX 1000 manufactured by Toyo ADL Corporation, with a melting point of 99° C., and a needle penetration of 2 at 25° C.) (14 parts by mass), an ethylene/vinyl acetate copolymer (EV-150 manufactured by Du Pont-Mitsui Polychemicals Co., Ltd., with a weight average molecular weight of 2,100, and VAc of 21%) (6 parts by mass), toluene (60 parts by mass), and methyl ethyl ketone (20 parts by mass) were dispersed until the average particle diameter became 2.5 µm, to thereby obtain a release layer coating liquid.

3. Preparation of Solid Reagent Phase Layer Coating Liquid
3-1. Fixing

A polyvinyl butyral resin (BL-10 manufactured by Sekisui Chemical Co., Ltd., with a butyralation degree of 72 mol %) (5 parts by mass), and ethanol (95 parts by mass) were mixed, to thereby obtain a fixing-purpose solid reagent phase layer coating liquid.

3-2. Release

A polyvinyl butyral resin (BL-1 manufactured by Sekisui Chemical Co., Ltd., with a butyralation degree of 64 mol %) (5 parts by mass), and ethanol (95 parts by mass) were mixed, to thereby obtain a release-purpose solid reagent phase layer coating liquid.

4. Preparation of Reagent Coating Liquid
4-1. Test Line

An antibody dilution buffer (Dulbecco's phosphate buffered saline D8662 manufactured by Sigma Aldrich Co., LLC.) was added to an anti-human IgG antibody (I1886 manufactured by Sigma Co.) such that the antibody would be prepared to be 0.9 mg/mL, to thereby obtain a test line reagent coating liquid.

4-2. Control Line

An antibody dilution buffer was added to human IgG (12511-10MG manufactured by Sigma Co.) such that the antibody would be prepared to be 0.9 mg/mL, to thereby obtain a control line reagent coating liquid.

4-3. Labeled Antibody

A gold colloid-labeled anti-human IgG antibody (manufactured by BAW Inc., gold, an average particle diameter of 40 nm, and OD=15) was diluted with a gold colloid coating liquid (a 20 mM tris-HCl buffer (with pH of 8.2), 0.05% by mass polyethylene glycol, and 5% by mass sucrose) and purified water, such that it would be prepared to be OD=10, to thereby obtain a labeled antibody reagent coating liquid.

<Layer Formation>
1. Formation of Back Layer

The back layer coating liquid was applied to one surface of a support member, which was a polyethylene terephthalate (PET) film (LUMIRROR F57 manufactured by Toray Industries, Inc.) having an average thickness of 4.5 µm, and dried at 80° C. for 10 seconds, to thereby form a back layer having an average thickness of 0.02 µm.

2. Formation of Release Layer

Next, the release layer coating liquid was applied over a surface of the PET film opposite to the surface over which the back layer was formed, and dried at 50° C. for 180 seconds, to thereby form a release layer having an average thickness of 85 μm.

3-1. Test Line Thermal Transfer Member and Control Line Thermal Transfer Member

Next, the fixing-purpose solid reagent phase layer coating liquid was applied over the release layer, and dried at 70° C. for 60 seconds, to thereby form a solid reagent phase layer having an average thickness of 5 μm. Then, the test line reagent coating liquid was applied over the solid reagent phase layer, and dried at 25° C. for 5 hours, to thereby form the reagent as a solid phase over the solid reagent phase layer. In this way, a test line thermal transfer member was obtained.

In the same manner as described above, the fixing-purpose solid reagent phase layer coating liquid was applied over the release layer, and dried at 70° C. for 60 seconds, to thereby form a solid reagent phase layer having an average thickness of 5 μm. Then, the control line reagent coating liquid was applied over the solid reagent phase layer, and dried at 25° C. for 5 hours, to thereby form the reagent as a solid phase over the solid reagent phase layer. In this way, a control line thermal transfer member was obtained.

3-2. Labeled Antibody Thermal Transfer Member

A back layer and a release layer were formed in the manner described above. After this, the release-purpose solid reagent phase layer coating liquid was applied over the release layer, and dried at 70° C. for 60 seconds, to thereby form a solid reagent phase layer having an average thickness of 5 μm. Then, the labeled antibody reagent coating liquid was applied over the solid reagent phase layer in an amount of 12 μL/cm$^2$, and dried at 25° C. for 5 hours, to thereby form a labeled antibody layer over the solid reagent phase layer. In this way, a labeled antibody thermal transfer member was obtained.

<<Fabrication of Testing Device>>
<Production of Paper Substrate>

A thermoplastic resin, which was a polyester-based hot-melt adhesive (ALONMELT PES375S40 manufactured by Toagosei Co., Ltd.), was heated to 190° C., and then with a roll coater, applied over a PET film (LUMIRROR S10 manufactured by Toray Industries, Inc., with an average thickness of 50 μm) cut into a size of 40 mm in width and 80 mm in length, to have a thickness of 50 μm over the PET film, to thereby form an adhesive layer. This applied product was kept stationary for 2 hours or longer. After this, each of the materials shown in Table 1, each of which was cut into a size of 40 mm in width and 70 mm in length, was overlapped with the adhesive layer-applied surface such that a longer-direction one end of each of the materials (this end was defined as an upstream end, and the opposite end was defined as a downstream end) would coincide with a longer-direction one end of the adhesive layer-applied surface. Then, a load of 1 kgf/cm$^2$ was applied to them at 150° C. for 10 seconds. Finally, the obtained product was cut along the longer direction thereof, into a size of 4 mm in width and 80 mm in length, to thereby obtain paper substrates A to E.

The voidage of the paper substrates A to E was calculated according to the calculation formula 1 below, based on the basis weight (g/m$^2$) and the thickness (μm) of the paper substrates, and the specific gravity of the component thereof.

Voidage (%)={1−[basis weight (g/m$^2$)/thickness (μm)/specific gravity of the component]}×100     [Calculation Formula 1]

If the voidage of the paper substrates were in a range of from 40% to 90%, the paper substrates could be said to be porous. From the results in Table 1 below, all of the paper substrates A to E were porous.

TABLE 1

| | Kind of paper substrate | Brand, and Name of manufacturer | Voidage (%) |
|---|---|---|---|
| A | Nitrocellulose membrane filter | HF240, Merck Millipore Corporation | 70 |
| B | Hydrophilic PTFE (polytetrafluoroethylene) | JMWP 14225, Merck Millipore Corporation | 80 |
| C | Hydrophilic PVDF (polyvinylidene fluoride) | SVLP 04700, Merck Millipore Corporation | 70 |
| D | Qualitative filter | Qualitative filter No. 4A, Advantec, Co., Ltd. | 48 |
| E | Groundwood paper | TA-914, Maruai Inc. | 70 |

<Transfer of Reagent>
1. Labeled Antibody

Figure 10A:
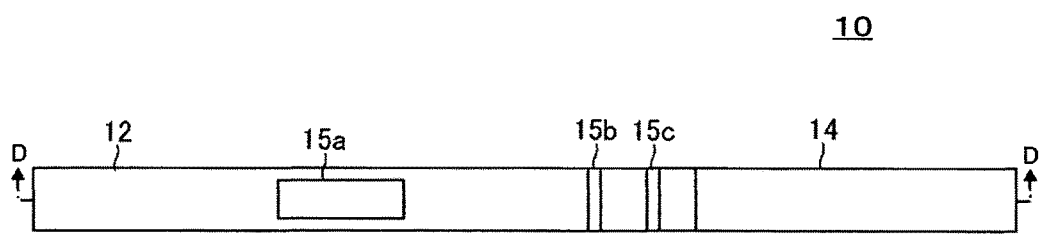
FIG. 10A is an exemplary diagram of a testing device of Example.
Figure 10B:
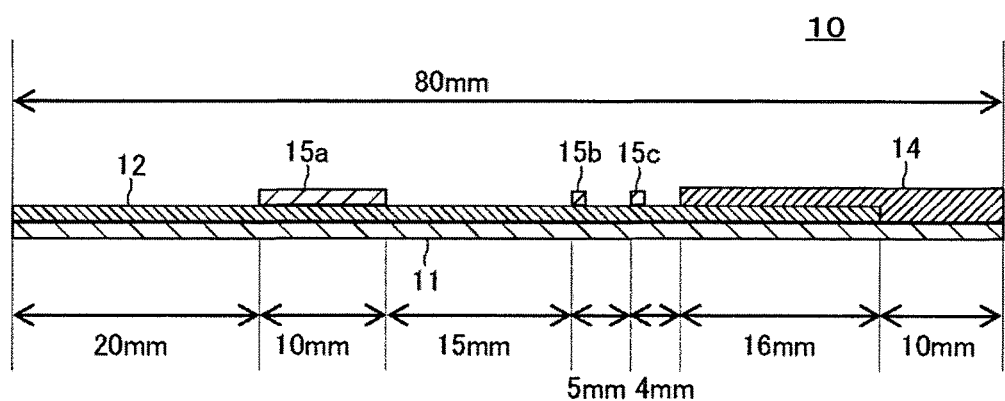
FIG. 10B is an exemplary diagram of a testing device of Example.

Each of the paper substrates A to E was overlapped with a surface of the reagent thermal transfer member over which the reagent was formed as a solid phase. After this, with a thermal transfer printer, the labeled antibody thermal transfer member was transferred onto the paper substrate at a position that was 20 mm away from an upstream end of the paper substrate to form a pattern having a size of 3 mm in width and 10 mm in length, as shown in FIG. 10A and FIG. 10B. FIG. 10A is a top plan view of a testing device of Example. FIG. 10B is a cross-sectional diagram of the testing device of FIG. 10A taken along a line D-D. For the pattern formation printing, a thermal head having a dot density of 300 dpi (manufactured by TDK Corporation) was used at a printing speed of 42 mm/sec and at a printing energy of 0.17 mJ/dot, and constructed as an evaluation system for evaluation of the printing.

2. Test Line and Control Line

The test line thermal transfer member was transferred onto a position that was 15 mm away from the position to which the labeled antibody thermal transfer member was transferred, to form a line shape having a width of 0.7 mm and a length of 4 mm, as shown in FIG. 10A and FIG. 10B. Then, the control line thermal transfer member was transferred onto a position that was 5 mm away from the test line thermal transfer member, to form a line shape having a width of 0.7 mm and a length of 4 mm. These lines were formed under the same printing conditions as described above.

3. Absorbent Member

Then, the absorbent member 14 (CFSP 223000 manufactured by Merck Millipore Corporation) was provided as shown in FIG. 10A and FIG. 10B, to thereby obtain immunochromatography assays (testing devices 10) A to E of Example 1.

[1] Line Visibility Evaluation
<<Evaluation Method>>
1. Preparation of Test Liquid An antibody dilution buffer (Dulbecco's phosphate buffered saline D8662 manufactured by Sigma Aldrich Co., LLC.) was added to human IgG such that the human IgG would be prepared to be 500 μg/mL, to thereby obtain a test liquid.

2. Reaction

The test liquid (100 μL) was dropped into the upstream end portion of the immunochromatography assays A to E. Thirty minutes later, the immunochromatography assays were observed. Any of them in which color development could be clearly recognized at the positions of the test line and the control line, and the color development had a uniform density all along and was continuous as lines was evaluated as A. Any of them in which color development was continuous as lines to suffice for determination, but had some density variations from place to place was evaluated as B. Any of them in which color development could be recognized narrowly and formed lines, but the lines were discontinuous partially was evaluated as C. Any of them in which color development was not in line shapes, such as a case where no color development could be recognized, or a case where lines flowed to the downstream side was evaluated as D. Examples of the evaluation criteria are shown in Table 2. The images in Table 2 were images of the test lines after the testing. The configurations of the immunochromatography assays are shown in FIG. 10A and FIG. 10B, and evaluation results are shown in Table 4a and Tables 4b-1 and 4b-2.

[2] Measurement of Color Development Density at Lines

The immunochromatography assays after the color development, which were used in [1], were put into a housing case for measurement, and measured with a chromato-reader (DIASCAN 10 manufactured by Otsuka Electronics Co., Ltd.) to obtain an optical density of the lines. A higher optical density is more preferable. In the case of immunochromatography assays, those having an optical density of 250 or higher were evaluated as A, those having an optical density of 150 or higher but lower than 250 were evaluated as B, those having an optical density of 50 or higher but lower than 150 were evaluated as C, and those that had an optical density of lower than 50 or could not be measured because no lines could be recognized were evaluated as D. In the case of chemical assays, those having an optical density of 400 or higher were evaluated as A, those having an optical density of 250 or higher but lower than 400 were evaluated as B, those having an optical density of 100 or higher but lower than 250 were evaluated as C, and those that had an optical density of lower than 100 or could not be measured because no lines could be recognized were evaluated as D. Evaluation results are shown in Table 4a and Tables 4b-1 and 4b-2.

Example 2

Immunochromatography assays A to E of Example 2 were fabricated in the same manner as in Example 1, except that the polyvinyl butyral resin used for the fixing-purpose solid reagent phase layer coating liquid in Example 1 was changed to a polyvinyl acetal resin (KS-10 manufactured by Sekisui Chemical Co., Ltd., with an acetalation degree of 78 mol %), and the polyvinyl butyral resin used for the release-purpose solid reagent phase layer coating liquid in Example 1 was changed to a polyvinyl butyral resin (a mixed type having an acetoacetal group and a butyral group) (BX-L manufactured by Sekisui Chemical Co., Ltd., with an acetalation degree of 63±3 mol %).

The fabricated immunochromatography assays A to E were evaluated in the same manner as in Example 1. The results are shown in Table 4a and Tables 4b-1 and 4b-2.

Example 3

Immunochromatography assays A to E of Example 3 were fabricated in the same manner as in Example 1, except that the anti-human IgG antibody used for the test line reagent coating liquid in Example 1 was changed to an anti-hCG monoclonal antibody (ANTI-ALPHA SUBUNIT 6601 SPR-5 manufactured by Medix Biochemica Inc.), human IgG used for the control line reagent coating liquid in Example 1 was changed to an anti-mouse IgG antibody (566-70621 manufactured by Wako Pure Chemical Industries, Ltd.), and the gold colloid-labeled anti-human IgG antibody used for the labeled antibody reagent coating liquid in Example 1 was changed to a gold colloid-labeled antibody produced in the manner described below.

<Production of Labeled Antibody Reagent Coating Liquid>

A $KH_2PO_4$ buffer (pH of 7.0) that was prepared to be 50 mM was added in an amount of 1 mL to a gold colloid solution (EMGC50 manufactured by BBI Solutions Inc.) (90 mL). After this, an anti-hCG monoclonal antibody (ANTI-HCG 5008 SP-5 manufactured by Medix Biochemica Inc.) that was prepared to be 50 µg/mL was added thereto in an amount of 1 mL, and they were stirred. After the resultant was kept stationary for 10 minutes, a 1% by mass polyethylene glycol aqueous solution (168-11285 manufactured by Wako Pure Chemical Industries, Ltd.) was added thereto in an amount of 550 µl, and they were stirred. After this, a 10% by mass BSA aqueous solution (A-7906 manufactured by Sigma Aldrich Co., LLC.) was added thereto in an amount of 1.1 mL, and they were stirred.

Next, the obtained solution was centrifuged for 30 minutes, and from which, a supernatant was removed except for about 1 mL of the supernatant. The resultant was treated with an ultrasonic cleaner to redisperse the gold colloid. The centrifugation was performed with a centrifuge (HIMAC CF16RN manufactured by Hitachi Koki Co., Ltd.), at a centrifugal acceleration of 8,000×g, and at 4° C. The resultant was dispersed in a gold colloid preservation liquid (a 20 mM tris-HCl buffer (pH of 8.2), 0.05% by mass polyethylene glycol, 150 mM NaCl, a 1% by mass BSA aqueous solution, and a 0.1% by mass $NaN_3$ aqueous solution) (20 mL), and again centrifuged under the same conditions as described above. From which, a supernatant was removed except for about 1 mL of the supernatant. The resultant was treated with an ultrasonic cleaner to redisperse the gold colloid, to thereby obtain a gold colloid-labeled antibody. After this, the produced gold colloid-labeled antibody was diluted with a gold colloid coating liquid and purified water such that it would be prepared to be OD=10, to thereby obtain a labeled antibody reagent coating liquid.

[1] Line Visibility Evaluation

<Evaluation Method>

1. Preparation of Test Liquid

An antibody dilution buffer (Dulbecco's phosphate buffered saline D8662 manufactured by Sigma Aldrich Co., LLC.) was added to hCG (recombinant hCG, 7727-CG-010 manufactured by R&D Systems, Inc.), such that hCG would be prepared to be 50 mIU/mL, to thereby obtain a test liquid.

2. Reaction

The test liquid (100 µL) was dropped into the upstream end portion of the immunochromatography assays A to E. Thirty minutes later, the immunochromatography assays were observed. Any of them in which color development could be clearly recognized at the positions of the test line and the control line, and the color development had a uniform density all along and was continuous as lines was evaluated as A. Any of them in which color development was continuous as lines to suffice for determination, but had some density variations from place to place was evaluated as B. Any of them in which color development could be recognized narrowly and formed lines, but the lines were discontinuous partially was evaluated as C. Any of them in which color development was not in line shapes, such as a case where no color development could be recognized, or a case where lines flowed to the downstream side was evaluated as D. Evaluation results are shown in Table 4a and Tables 4b-1 and 4b-2.

[2] Measurement of Color Development Density at Lines

Optical densities of the lines were measured in the same manner as in Example 1. Evaluation results are shown in Table 4a and Tables 4b-1 and 4b-2.

Example 4

<<Production of Reagent Thermal Transfer Member>>
<Preparation of Solution>
1. Preparation of Solid Reagent Phase Layer Coating Liquid
1-1. Fixing Polystyrene (POLYSTYRENE 331651-25G manufactured by Sigma Aldrich Co., LLC.) (5 parts by mass), and toluene (95 parts by mass) were mixed, to thereby obtain a fixing-purpose solid reagent phase layer coating liquid.

1-2. Release

A polyvinyl butyral resin (BL-1 manufactured by Sekisui Chemical Co., Ltd., with a butyralation degree of 64 mol %) (5 parts by mass), and ethanol (95 parts by mass) were mixed, to thereby obtain a release-purpose solid reagent phase layer coating liquid.

2. Preparation of Reagent Coating Liquid
2-1. Test Line

An antibody dilution buffer (Dulbecco's phosphate buffered saline D8662 manufactured by Sigma Aldrich Co., LLC.) was added to an anti-human IgG antibody (I1886 manufactured by Sigma Co.), such that the antibody would be prepared to be 10 μg/mL, to thereby obtain a test line reagent coating liquid.

2-2. Control Line

An antibody dilution buffer was added to human IgG (I2511-10MG manufactured by Sigma Aldrich Co., LLC.), such that the human IgG would be prepared to be 10 μg/mL, to thereby obtain a control line reagent coating liquid.

2-3. Labeled Antibody

A labeled antibody reagent coating liquid was obtained in the same manner as in Example 1.

<Layer Formation>
1. Formation of Back Layer

In the same manner as in Example 1, a back layer having an average thickness of 0.02 μm was formed over one surface of a PET film (LUMIRROR F57 manufactured by Toray Industries, Inc.) having an average thickness of 4.5 μm.

2. Formation of Release Layer

In the same manner as in Example 1, a release layer having an average thickness of 85 μm was formed.

3-1. Test Line Thermal Transfer Member and Control Line Thermal Transfer Member

Next, the fixing-purpose solid reagent phase layer coating liquid was applied over the release layer, and dried at 70° C. for 60 seconds, to thereby form a solid reagent phase layer (resin layer) having an average thickness of 5 μm. Then, the test line reagent coating liquid was applied over the solid reagent phase layer in an amount of 100 μL per unit area (cm$^2$), to form a water film. After this, the thermal transfer member was set in a container maintained to a relative humidity of 80% so as not to let the water film dry, and kept stationary at 37° C. for 1 hour. After the stationary keeping, the surface of the solid reagent phase layer was washed with an antibody dilution buffer, and dried in a vacuum dryer at 25° C. for 1 hour, to thereby form the reagent as a solid phase over the solid reagent phase layer. In this way, a test line thermal transfer member was obtained.

Further, in the same manner as described above, the fixing-purpose solid reagent phase layer coating liquid was applied over the release layer, and dried at 70° C. for 60 seconds, to thereby form a solid reagent phase layer (resin layer) having an average thickness of 5 μm. Then, in the same manner as for the test line, the control line reagent coating liquid was coated over the solid reagent phase layer and kept stationary, and then the surface of the solid reagent phase layer was washed and dried, to thereby form the reagent as a solid phase over the solid reagent phase layer. In this way, a control line thermal transfer member was obtained.

3-2. Labeled Antibody Thermal Transfer Member

A labeled antibody thermal transfer member was obtained in the same manner as in Example 1.

<Fabrication of Testing Device>

In the same manner as in Example 1, a labeled antibody, a test line, and a control line were formed over the paper substrates A to E and an absorption pad was placed, to thereby obtain immunochromatography assays (testing devices 10) A to E of Example 4. Visibility and density were evaluated in the same manner as in Example 1. The results are shown in Table 4a and Tables 4b-1 and 4b-2.

Example 5

In production of a fixing-purpose solid reagent phase layer coating liquid, carnauba wax (manufactured by Nihon Wax Corporation, carnauba wax, specially-made product No. 2) (10 parts by mass), and toluene/methyl ethyl ketone (3/1) (90 parts by mass) were mixed, to thereby obtain a fixing-purpose solid reagent phase layer coating liquid.

Immunochromatography assays (testing devices 10) A to E of Example 5 were obtained in the same manner as in Example 4, except for the operation described just above. Visibility and density were evaluated in the same manner as in Example 1. The results are shown in Table 4a and Tables 4b-1 and 4b-2.

Example 6

In production of a fixing-purpose solid reagent phase layer coating liquid, polyethylene wax (POLYWAX 1000 manufactured by Toyo ADL Corporation) (5 parts by mass), and toluene (95 parts by mass) were mixed, to thereby obtain a fixing-purpose solid reagent phase layer coating liquid.

Immunochromatography assays (testing devices 10) A to E of Example 6 were obtained in the same manner as in Example 4, except for the operation described just above. Visibility and density were evaluated in the same manner as in Example 1. The results are shown in Table 4a and Tables 4b-1 and 4b-2.

Comparative Example 1

1. Preparation of Reagent Coating Liquid
1-1. Test Line

An antibody dilution buffer was added to an anti-human IgG antibody such that the antibody would be prepared to be 0.9 mg/mL, to thereby obtain a test line reagent coating liquid.

1-2. Control Line

An antibody dilution buffer was added to human IgG, such that the human IgG would be prepared to be 0.9 mg/mL, to thereby obtain a control line reagent coating liquid.

1-3. Labeled Antibody

A labeled antibody dilution buffer was added to a gold colloid-labeled anti-human IgG antibody such that the antibody would be prepared to be OD=2, to thereby obtain a labeled antibody reagent coating liquid.

2. Production of Assay Member

<Production of Paper Substrate>

A thermoplastic resin, which was a polyester-based hot-melt adhesive (ALONMELT PES375S40 manufactured by Toagosei Co., Ltd.), was heated to 190° C., and then with a roll coater, applied over a PET film (LUMIRROR S10 manufactured by Toray Industries, Inc., with an average thickness of 50 µm) cut into a size of 40 mm in width and 35 mm in length, to have a thickness of 50 µm over the PET film, to thereby form an adhesive layer. This applied product was kept stationary for 2 hours or longer. After this, each of the materials shown in Table 1, each of which was cut into the same size as the PET film, was overlapped with the adhesive layer-applied surface. Then, a load of 1 kgf/cm² was applied to them at 150° C. for 10 seconds, to thereby obtain paper substrates A to E.

<Formation of Reagent as Solid Phase>

Figure 11A:
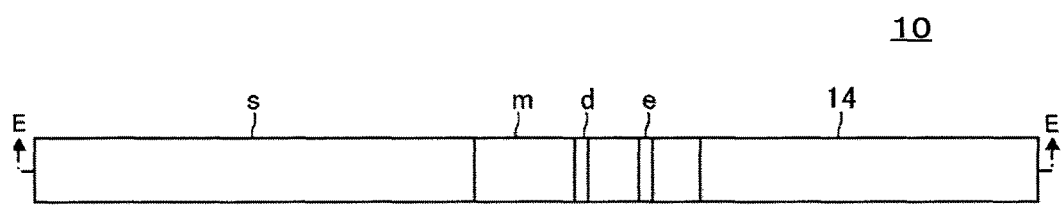
FIG. 11A is an exemplary diagram of a testing device of Comparative Example.
Figure 11B:
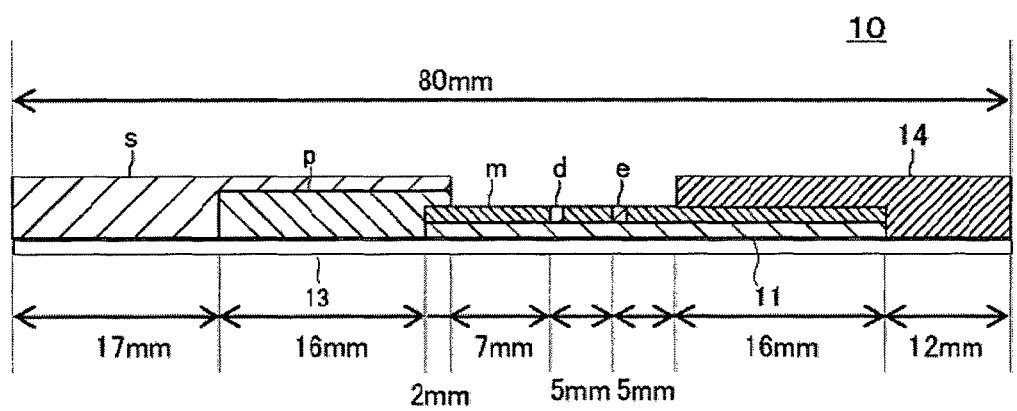
FIG. 11B is an exemplary diagram of a testing device of Comparative Example.

With a positive-pressure spray device (BIOJET manufactured by BioDot Inc.), the test line reagent coating liquid was applied over each of the paper substrates A to E at a position d that was 9 mm away from a shorter-direction one end of the paper substrates, to form a line shape having a width of 0.7 mm, as shown in FIG. 11A and FIG. 11B. FIG. 11A is a top plan view of a testing device of Comparative Example 1. FIG. 11B is a cross-sectional diagram of the testing device of FIG. 11A taken along a line E-E. Then, with the positive-pressure spray device, the control line reagent coating liquid was applied at a position e that was 5 mm away from the position d, to form a line shape having a width of 0.7 mm. After the application, the coating liquids were dried at 20° C. at −20 RH % for 16 hours.

<Production of Labeled Antibody Retaining Pad>

The labeled antibody solution produced in 1-3 was applied in an amount of 60 µL/cm² over a glass fiber pad (GFCP 203000 manufactured by Merck Millipore Corporation, p in FIG. 11A and FIG. 11B) cut into a size of 40 mm in width and 18 mm in length, and dried at reduced pressure for one night, to thereby produce a labeled antibody retaining pad.

3. Assembly of Assay

Each of the paper substrates A to E was bonded to a PET film (LUMIRROR S10 manufactured by Toray Industries, Inc., with an average thickness of 100 µm), which was a base film cut into a size of 40 mm in width and 80 mm in length, at a position that was 33 mm away from a longer-direction one end of the base film (PET film), such that a surface of the paper substrate opposite to the surface thereof over which the reagents were applied would face the base film (PET film).

Next, the labeled antibody retaining pad produced as above, which was cut into a size of 40 mm in width and 18 mm in length, was pasted over the top surface of the paper substrate such that it would overlap with the upstream end of the paper substrate by 2 mm. Further, a sample pad (CFSP 223000 manufactured by Merck Millipore Corporation, s in FIG. 11A and FIG. 11B) having a size of 40 mm in width and 35 mm in length was pasted such that it would overlap with the top surface of the labeled antibody retaining pad by 18 mm, and would be used as a sample dropping pad. Next, an absorption pad having a size of 40 mm in width and 28 mm in length was pasted over the top surface of the paper substrate such that it would overlap with the downstream end of the paper substrate by 16 mm, and would be provided as the absorbent member 14 (CFSP 223000 manufactured by Merck Millipore Corporation). Finally, the obtained product was cut along the longer direction thereof into a size of 4 mm in width and 80 mm in length, to thereby obtain immunochromatography assays (testing devices 10) A to E of Comparative Example 1.

The fabricated immunochromatography assays A to E were evaluated in the same manner as in Example 1. The results are shown in Table 4a and Tables 4b-1 and 4b-2.

Comparative Example 2

Immunochromatography assays A to E of Comparative Example 2 were fabricated in the same manner as in Comparative Example 1, except that the anti-human IgG antibody used for the test line reagent coating liquid in Comparative Example 1 was changed to an anti-hCG monoclonal antibody (ANTI-ALPHA SUBUNIT 6601 SPR-5 manufactured by Medix Biochemica Inc.), human IgG (I2511-10MG manufactured by Sigma Aldrich Co., LLC.) used for the control line reagent coating liquid in Comparative Example 1 was changed to an anti-mouse IgG antibody (566-70621 manufactured by Wako Pure Chemical Industries, Ltd.), and the gold colloid-labeled anti-human IgG antibody used for the labeled antibody reagent coating liquid in Comparative Example 1 was changed to the gold colloid-labeled antibody produced in Example 3.

The fabricated immunochromatography assays A to E were evaluated in the same manner as in Example 3. The results are shown in Table 4a and Tables 4b-1 and 4b-2.

TABLE 3

| | | Fixing resin | | | Release resin | | |
|---|---|---|---|---|---|---|---|
| | Antibody | Kind of resin | Product type | Hydrophobic group (mol %) | Kind of resin | Product type | Hydrophobic group (mol %) |
| Ex. 1 | IgG | Polyvinyl butyral | BL-10 | 72 | Polyvinyl butyral | BL-1 | 64 |
| Ex. 2 | IgG | Polyvinyl acetal | KS-10 | 78 | Polyvinyl butyral resin (mixed type having acetoacetal group and butyral group) | BX-L | 63 ± 3 |
| Ex. 3 | hCG | Polyvinyl butyral | BL-10 | 72 | Polyvinyl butyral | BL-1 | 64 |
| Ex. 4 | IgG | Polystyrene | 331651-25G | 100 | Polyvinyl butyral | BL-1 | 64 |

TABLE 3-continued

| | | Fixing resin | | | Release resin | | |
|---|---|---|---|---|---|---|---|
| | Antibody | Kind of resin | Product type | Hydrophobic group (mol %) | Kind of resin | Product type | Hydrophobic group (mol %) |
| Ex. 5 | IgG | Carnauba wax | Specially-made product No. 2 | 94 | Polyvinyl butyral | BL-1 | 64 |
| Ex. 6 | IgG | Polyethylene wax | POLYWAX 1000 | 100 | Polyvinyl butyral | BL-1 | 64 |
| Comp. Ex. 1 | IgG | — | — | — | — | — | — |
| Comp. Ex. 2 | hCG | — | — | — | — | — | — |

TABLE 4A

| | Evaluation of visibility | | | | |
|---|---|---|---|---|---|
| Paper substrate material | A Nitrocellulose | B Hydrophilic PTFE | C Hydrophilic PVDF | D Qualitative filter | E Groundwood paper |
| Ex. 1 | A | A | A | B | B |
| Ex. 2 | A | A | A | B | B |
| Ex. 3 | A | A | A | B | B |
| Ex. 4 | A | A | A | A | A |
| Ex. 5 | A | A | A | A | A |
| Ex. 6 | A | A | A | A | A |
| Comp. Ex. 1 | B | C | C | D | D |
| Comp. Ex. 2 | B | C | C | D | D |

TABLE 4b-1

| | Evaluation of density | | | | | |
|---|---|---|---|---|---|---|
| Paper substrate material | A Nitrocellulose | | B Hydrophilic PTFE | | C Hydrophilic PVDF | |
| | Reading | Evaluation | Reading | Evaluation | Reading | Evaluation |
| Ex. 1 | 218 | B | 222 | B | 220 | B |
| Ex. 2 | 215 | B | 223 | B | 223 | B |
| Ex. 3 | 223 | B | 215 | B | 214 | B |
| Ex. 4 | 288 | A | 292 | A | 294 | A |
| Ex. 5 | 293 | A | 283 | A | 289 | A |
| Ex. 6 | 285 | A | 291 | A | 290 | A |
| Comp. Ex. 1 | 217 | B | 74 | C | 85 | C |
| Comp. Ex. 2 | 220 | B | 71 | C | 79 | C |

TABLE 4b-2

| | Evaluation of density | | | |
|---|---|---|---|---|
| Paper substrate material | D Qualitative filter | | E Groundwood paper | |
| | Reading | Evaluation | Reading | Evaluation |
| Ex. 1 | 217 | B | 223 | B |
| Ex. 2 | 216 | B | 221 | B |
| Ex. 3 | 224 | B | 216 | B |
| Ex. 4 | 292 | A | 293 | A |
| Ex. 5 | 286 | A | 284 | A |
| Ex. 6 | 291 | A | 292 | A |
| Comp. Ex. 1 | Unmeasurable | D | Unmeasurable | D |
| Comp. Ex. 2 | Unmeasurable | D | Unmeasurable | D |

In Examples 1 to 6, color development in lines could be recognized in all of the immunochromatography assays formed of the paper substrates A to E in the evaluation of visibility (Table 4a). Particularly, clear lines could be recognized in A to C. Above all, in Examples 4 to 6, highly visible lines having a uniform color development density all along could be recognized. Further, lines having a high density could be recognized in all of the immunochromatography assays formed of the paper substrates A to E in the evaluation of optical density (Tables 4b-1 and 4b-2). Above all, in Examples 4 to 6, particularly dense lines of which density was 250 or higher on the reading basis could be recognized.

On the other hand, in Comparative Examples 1 and 2, although color development that was continuous as lines could be recognized in the paper substrates A, bleeding was heavy at the lines and color development could only be recognized narrowly in the paper substrates B and C, and non-specific adsorption to the paper substrates was heavy all over the substrates and no lines could be recognized in the paper substrates D and E in the evaluation of visibility. Further, in the evaluation of optical density, although a density higher than 200 on the reading basis could be observed in the paper substrates A, color development was blurred and resulted in a low density in the paper substrates B and C because labeling particles in the lines were spread through the paper, and color development was unmeasurable in the paper substrates D and E because it was blurred so heavily that no line shapes could be recognized.

Example 7

(Fabrication of Chemical Assay)
<<Production of Reagent Thermal Transfer Member>>
<Preparation of Solution>
1. Preparation of Back Layer Coating Liquid
A silicone-based rubber emulsion (KS779H manufactured by Shin-Etsu Chemical Co., Ltd., with a solid content of 30% by mass) (16.8 parts by mass), a chloroplatinic acid catalyst (0.2 parts by mass), and toluene (83 parts by mass) were mixed, to thereby obtain a back layer coating liquid.

2. Preparation of Release Layer Coating Liquid

A polyethylene wax (POLYWAX 1000 manufactured by Toyo ADL Corporation, with a melting point of 99° C., and a needle penetration of 2 at 25° C.) (14 parts by mass), an ethylene/vinyl acetate copolymer (EV-150 manufactured by Du Pont-Mitsui Polychemicals Co., Ltd., with a weight average molecular weight of 2,100, and VAc of 21%) (6 parts by mass), toluene (60 parts by mass), and methyl ethyl ketone (20 parts by mass) were dispersed until the average particle diameter became 2.5 µm, to thereby obtain a release layer coating liquid.

3. Preparation of Solid Reagent Phase Layer Coating Liquid 3-1. Fixing

A polyvinyl butyral resin (BL-10 manufactured by Sekisui Chemical Co., Ltd., with a butyralation degree of 72 mol %) (5 parts by mass), and ethanol (95 parts by mass) were mixed, to thereby obtain a fixing-purpose solid reagent phase layer coating liquid.

4. Preparation of Reagent Coating Liquid 4-1. Sensing Line 3,5-di-tert-butyl salicylic acid (149136-5G manufactured by Sigma Aldrich Co., LLC.) (5 parts by mass), sodium hydroxide (306576-25G manufactured by Sigma Aldrich Co., LLC.) (0.8 parts by mass), and distilled water (32 parts by mass) were mixed and stirred sufficiently, to make a 3,5-di-tert-butyl salicylic acid sodium salt aqueous solution, to thereby obtain a sensing line reagent coating liquid.

<Layer Formation>

1. Formation of Back Layer

The back layer coating liquid was applied to one surface of a support member, which was a PET film (LUMIRROR F57 manufactured by Toray Industries, Inc.) having an average thickness of 4.5 µm, and dried at 80° C. for 10 seconds, to thereby form a back layer having an average thickness of 0.02 µm.

2. Formation of Release Layer

Next, the release layer coating liquid was applied over a surface of the PET film opposite to the surface over which the back layer was formed, and dried at 50° C. for 180 seconds, to thereby form a release layer having an average thickness of 85 µm.

3-1. Sensing Line Thermal Transfer Member

Next, the fixing-purpose solid reagent phase layer coating liquid was applied over the release layer, and dried at 70° C. for 60 seconds, to thereby form a solid reagent phase layer having an average thickness of 5 µm. Then, the sensing line reagent coating liquid was applied over the solid reagent phase layer, and dried at 25° C. for 5 hours, to thereby form the reagent as a solid phase over the solid reagent phase layer. In this way, a sensing line thermal transfer member was obtained.

<<Fabrication of Testing Device>>
<Production of Paper Substrate>

A thermoplastic resin, which was a polyester-based hot-melt adhesive (ALONMELT PES375S40 manufactured by Toagosei Co., Ltd.), was heated to 190° C., and then with a roll coater, applied over a PET film (LUMIRROR S10 manufactured by Toray Industries, Inc., with an average thickness of 50 µm) cut into a size of 40 mm in width and 80 mm in length, to have a thickness of 50 µm over the PET film, to thereby form an adhesive layer. This applied product was kept stationary for 2 hours or longer. After this, each of the materials shown in Table 1, each of which was cut into a size of 40 mm in width and 70 mm in length, was overlapped with the adhesive layer-applied surface such that a longer-direction one end of each of the materials (this end was defined as an upstream end, and the opposite end was defined as a downstream end) would coincide with a longer-direction one end of the adhesive layer-applied surface. Then, a load of 1 kgf/cm$^2$ was applied to them at 150° C. for 10 seconds. Finally, the obtained product was cut along the longer direction thereof, into a size of 4 mm in width and 80 mm in length, to thereby obtain paper substrates A to E.

<Transfer of Reagent>

1. Sensing Line

Figure 12A:
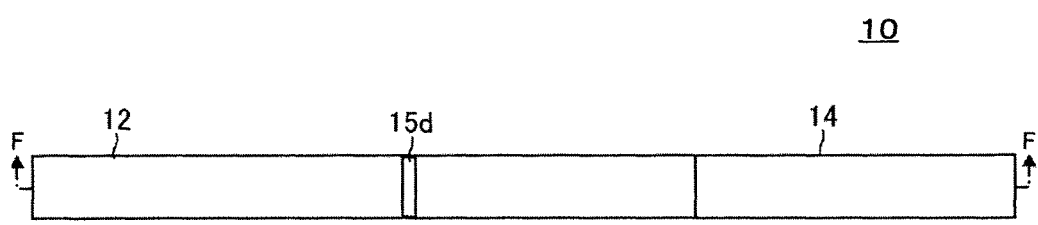
FIG. 12A is an exemplary diagram of a testing device of Example.
Figure 12B:
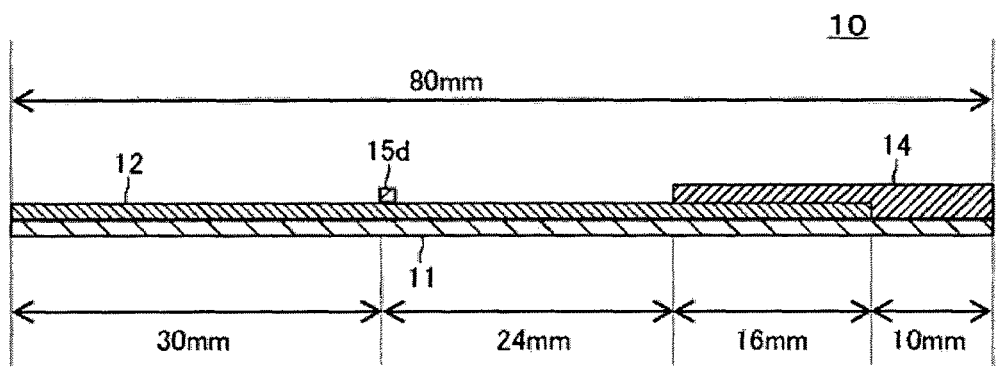
FIG. 12B is an exemplary diagram of a testing device of Example.

Each of the paper substrates A to E was overlapped with a surface of the reagent thermal transfer member over which the reagent was formed as a solid phase. After this, with a thermal transfer printer, the sensing line thermal transfer member was transferred onto the paper substrate at a position that was 30 mm away from an upstream end of the paper substrate to form a line shape having a size of 0.7 mm in width and 4 mm in length, to thereby form a resin layer 15$d$, as shown in FIG. 12A and FIG. 12B. FIG. 12A is a top plan view of a testing device of the Example. FIG. 12B is a cross-sectional diagram of the testing device of FIG. 12A taken along a line F-F. For the pattern formation printing, a thermal head having a dot density of 300 dpi (manufactured by TDK Corporation) was used at a printing speed of 42 mm/sec and at a printing energy of 0.17 mJ/dot, and constructed as an evaluation system for evaluation of the printing.

2. Absorbent Member

Then, the absorbent member 14 (CFSP 223000 manufactured by Merck Millipore Corporation) was provided as shown in FIG. 12A and FIG. 12B, to thereby obtain chemical assays (testing devices 10) A to E of Example 7.

<<Evaluation Method>>

1. Preparation of Test Liquid

Distilled water (58 parts by mass) was added to iron (III) chloride hexahydrate (012497 manufactured by Wako Pure Chemical Industries, Ltd.) (5 parts by mass), such that the iron (III) chloride hexahydrate would be prepared to be 5% by mass, to thereby obtain a test liquid.

2. Reaction

The test liquid (100 µl) was dropped into the upstream end portion of the chemical assays A to E. Ten minutes later, the chemical assays were observed, and determined based on the same evaluation criteria as in Example 1. The evaluation results are shown in Table 6a and Table 6b.

Comparative Example 3

<Formation of Reagent as Solid Phase>

Figure 13A:
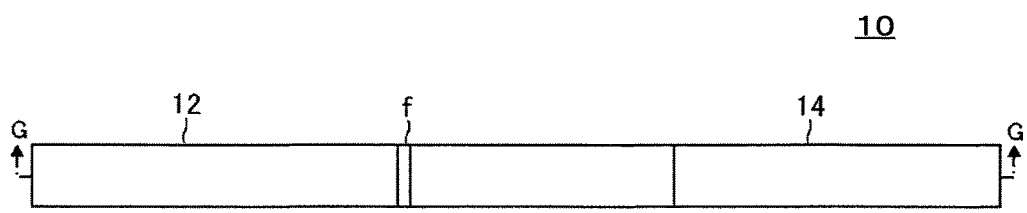
FIG. 13A is an exemplary diagram of a testing device of Comparative Example.
Figure 13B:
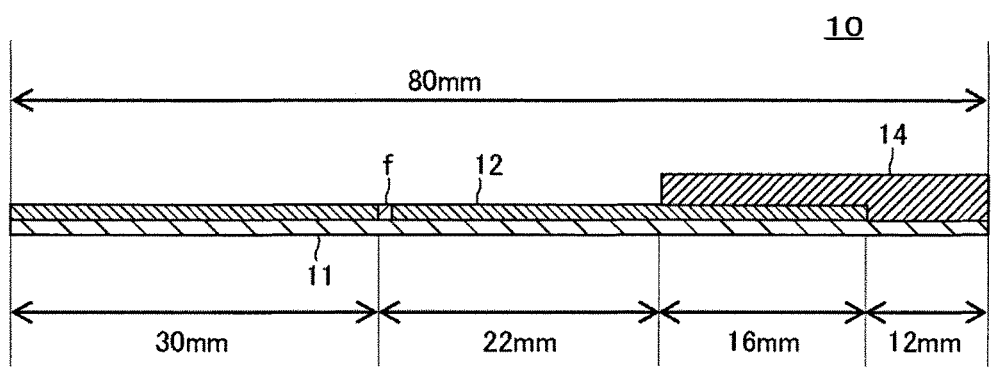
FIG. 13B is an exemplary diagram of a testing device of Comparative Example.
Figure 14:
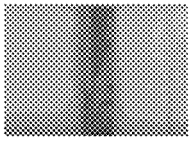
FIG. 14 shows Table 2 that provides examples of evaluation criteria based on images of test lines after testing.
Figure 14:
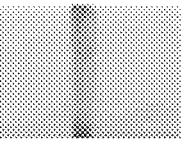
Figure 14:
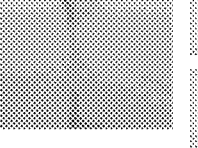
Figure 14:
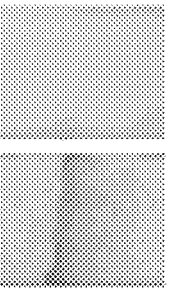

Instead of thermally transferring a sensing line onto the paper substrates A to E as in Example 7, with a positive-pressure spray device (BIOJET manufactured by BioDot Inc.), the sensing line reagent coating liquid was applied over the paper substrates A to E at a position f that was 30 mm away from a longer-direction one end of the paper substrates, to form a line shape having a width of 0.7 mm, as shown in FIG. 13A and FIG. 13B. FIG. 13A is a top plan view of a testing device of Comparative Example. FIG. 13B is a cross-sectional diagram of the testing device of FIG. 13A taken along a line G-G. After the application, the coating liquid was dried at 20° C. at −20 RH % for 16 hours.

Chemical assays (testing devices 10) A to E of Comparative Example 3 were obtained in the same manner as in Example 7, except for what is described above. The fabricated chemical assays A to E were evaluated in the same manner as in Example 7. The results are shown in Table 6a and Table 6b.

TABLE 5

| | Reagent | Fixing resin Kind of resin | Product type | Hydrophobic group (mol %) |
|---|---|---|---|---|
| Ex. 7 | Indicator | Polyvinyl butyral | BL-10 | 72 |
| Comp. Ex. 3 | Indicator | — | — | — |

TABLE 6a

Evaluation of visibility

| Paper substrate material | A Nitrocellulose | B Hydrophilic PTFE | C Hydrophilic PVDF | D Qualitative filter | E Groundwood paper |
|---|---|---|---|---|---|
| Ex. 7 | A | A | A | A | A |
| Comp. Ex. 3 | B | B | B | C | C |

TABLE 6b-1

Evaluation of density

| Paper substrate material | A Nitrocellulose Reading | Evaluation | B Hydrophilic PTFE Reading | Evaluation | C Hydrophilic PVDF Reading | Evaluation |
|---|---|---|---|---|---|---|
| Ex. 7 | 324 | B | 312 | B | 330 | B |
| Comp. Ex. 3 | 317 | B | 264 | B | 271 | B |

TABLE 6b-2

Evaluation of density

| Paper substrate material | D Qualitative filter Reading | Evaluation | E Groundwood paper Reading | Evaluation |
|---|---|---|---|---|
| Ex. 7 | 317 | B | 325 | B |
| Comp. Ex. 3 | 113 | C | 126 | C |

In Example 7, color development in lines was recognized in all of the chemical assays formed of the paper substrates A to E in the evaluation of visibility. Further, lines having a high density could be recognized in all of the chemical assays formed of the paper substrates A to E in the evaluation of optical density. On the other hand, in Comparative Example 3, although color development in line shapes could be recognized in the paper substrates A to C, bleeding was heavy at the lines and color development could only be recognized narrowly in the paper substrates D and E in the evaluation of visibility. Further, in the evaluation of optical density, although a density of 250 or higher on the reading basis could be observed in the paper substrates A to C, color development was blurred and pale in the paper substrates D and E.

Aspects of the present invention are as follows, for example.

<1> A testing device, including:
a porous flow path member in which a flow path for flowing a sample is formed; and
a resin layer provided at one position or a plurality of positions over the flow path member,
wherein a reagent reactive with the sample is provided as a solid phase over a surface of the resin layer facing the flow path member.

<2> The testing device according to <1>, including:
a first resin layer and a second resin layer that are provided over the flow path member,
wherein over surfaces of the first and second resin layers facing the flow path member, the reagent provided as a solid phase over the first resin layer is a capture antibody, and the reagent provided as a solid phase over the second resin layer is a labeled antibody.

<3> The testing device according to <2>, including:
a plurality of the first resin layer.

<4> The testing device according to <2> or <3>,
wherein the first resin layer contains a resin having a hydrophobic group.

<5> The testing device according to <4>,
wherein the resin having a hydrophobic group is a hydrophobic resin or a first amphiphilic resin.

<6> The testing device according to any one of <2> to <5>,
wherein the second resin layer contains a second amphiphilic resin.

<7> The testing device according to <6>,
wherein the first amphiphilic resin has more hydrophobic groups than the second amphiphilic resin does.

<8> The testing device according to any one of <1> to <7>,
wherein the resin layer contains a water-insoluble resin.

<9> The testing device according to any one of <1> to <8>,
wherein the resin layer is a non-porous member.

<10> A testing kit, including:
the testing device according to any one of <1> to <9>; and
a sample picking member configured to pick the sample, or a liquid for treating the sample, or both thereof.

<11> A transfer member for testing device fabrication, including:
a support member;
a release layer provided over the support member; and
a solid reagent phase layer provided over the release layer,
wherein a reagent reactive with a sample is provided as a solid phase over a surface of the solid reagent phase layer.

<12> A method for fabricating a testing device, including:
bringing the solid reagent phase layer of the transfer member according to <11> into contact with a porous flow path member, and transferring the solid reagent phase layer onto the flow path member.

<13> A testing method, including:
supplying a sample into the flow path member of the testing device according to any one of <1> to <9>; and
releasing the reagent provided as a solid phase over the resin layer from the resin layer, by bringing the reagent into contact with the sample.

<14> A testing method, including:
supplying a sample into the flow path member of the testing device according to any one of <1> to <9>, and
letting a portion of the sample be captured by the reagent provided as a solid phase over the resin layer.

REFERENCE SIGNS LIST 10 testing device
11 base material
12 flow path member 13 base film
14 absorbent member
15 resin layer
15a resin layer
15b resin layer
15c resin layer
16 labeled antibody (an example of a reagent)
17 capture antibody (an example of a reagent)
18 capture antibody (an example of a reagent)
30 test liquid (an example of a sample)
31 antigen
50 testing kit
51 sterilized cotton swab
52 dilution buffer
100 reagent transfer member (an example of a transfer member)
101 support member
102 release layer
103 solid reagent phase layer
104 back layer
151 amphiphilic resin
152 hydrophilic group
153 hydrophobic group
154 amphiphilic resin
155 hydrophobic resin

The invention claimed is:

1. A testing device, comprising:
a porous flow path member in which a flow path for flowing a sample is formed; and
at least a first resin layer and a second resin layer each comprising resin, wherein the first resin layer and the second resin layer are provided at a plurality of positions over the flow path member and wherein each of the resin layers comprises a surface facing the porous flow path member,
wherein:
the first resin layer comprises a capture antibody provided as a solid phase over the surface of the first resin layer facing the porous flow path member, wherein the capture antibody is fixed on the surface of the first resin layer; and
the second resin layer comprises a labeled antibody provided as a solid phase over the surface of the second resin layer facing the porous flow path member.

2. The testing device according to claim 1, further comprising: a plurality of the first resin layer.

3. The testing device according to claim 1, wherein the first resin layer comprises a resin having a hydrophobic group.

4. The testing device according to claim 3, wherein the resin having a hydrophobic group is a hydrophobic resin or a first amphiphilic resin.

5. The testing device according to claim 4, wherein the second resin layer comprises a second amphiphilic resin.

6. The testing device according to claim 5, wherein the first amphiphilic resin has more hydrophobic groups than the second amphiphilic resin.

7. The testing device according to claim 1, wherein the first resin layer comprises a water-insoluble resin.

8. The testing device according to claim 1, wherein the first and second resin layers are a non-porous members.

9. A testing kit, comprising:
the testing device of claim 1; and
a sample picking member configured to pick the sample, or a liquid for treating the sample, or both.

10. A testing method, comprising:
supplying a sample into the flow path member of the testing device of claim 1; and
releasing the labeled antibody from the second resin layer by contacting the labeled antibody with the sample.

11. A testing method, comprising:
supplying a sample into the flow path member of the testing device of claim 1, such that a portion of the sample is captured by the capture antibody fixed on the surface of the first resin layer.

* * * * *